United States Patent
Piomelli et al.

(10) Patent No.: US 9,745,255 B2
(45) Date of Patent: Aug. 29, 2017

(54) META-SUBSTITUTED BIPHENYL PERIPHERALLY RESTRICTED FAAH INHIBITORS

(71) Applicants: The Regents of the University of California, Oakland, CA (US); Fondazione Istituto Italiano di Tecnologia, Genoa (IT); Universita Degli Studi di Urbino "Carlo Bo", Urbino (IT); Universita Degli Studi di Parma, Parma (IT)

(72) Inventors: Daniele Piomelli, Irvine, CA (US); Guillermo Moreno-Sanz, Irvine, CA (US); Tiziano Bandiera, Gambolo (IT); Marco Mor, Ghedi (IT); Giorgio Tarzia, Petriano (IT)

(73) Assignees: The Regents of the University of California, Oakland, CA (US); Fondazione Istituto Italiano di Technologia, Genoa (IT); Universita Degli Studi di Urbino "Carlo Bo", Urbino (IT); Universita Degli Studi di Parma, Parma (IT)

( * ) Notice: Subject to any disclaimer, the term of this patent is extended or adjusted under 35 U.S.C. 154(b) by 130 days.

(21) Appl. No.: 14/183,073

(22) Filed: Feb. 18, 2014

(65) Prior Publication Data
US 2014/0288170 A1    Sep. 25, 2014

Related U.S. Application Data

(63) Continuation of application No. PCT/US2012/051478, filed on Aug. 17, 2012.

(60) Provisional application No. 61/525,636, filed on Aug. 19, 2011.

(51) Int. Cl.
C07C 271/56    (2006.01)
C07C 269/02    (2006.01)
C07D 309/14    (2006.01)

(52) U.S. Cl.
CPC .......... *C07C 271/56* (2013.01); *C07C 269/02* (2013.01); *C07D 309/14* (2013.01); C07C 2101/04 (2013.01); C07C 2101/08 (2013.01); C07C 2101/14 (2013.01)

(58) Field of Classification Search
CPC ............................ C07C 271/56; C07C 269/02
See application file for complete search history.

(56) References Cited

U.S. PATENT DOCUMENTS

| | | |
|---|---|---|
| 4,325,889 A | 4/1982 | Behre et al. |
| 4,458,066 A | 7/1984 | Caruthers et al. |
| 4,511,503 A | 4/1985 | Olsen et al. |
| 5,541,061 A | 7/1996 | Fodor et al. |
| 5,559,410 A | 9/1996 | Papazian et al. |
| 5,576,220 A | 11/1996 | Hudson et al. |
| 5,952,315 A | 9/1999 | Baker et al. |
| 5,962,012 A | 10/1999 | Lin et al. |
| 6,261,595 B1 | 7/2001 | Stanley et al. |
| 6,271,015 B1 | 8/2001 | Gilula et al. |
| 6,313,174 B1 | 11/2001 | Ottosen et al. |
| 6,326,156 B1 | 12/2001 | Civelli et al. |
| 6,344,474 B1 | 2/2002 | Maruani et al. |
| 6,403,573 B1 | 6/2002 | Leysen et al. |
| 7,192,975 B2 | 3/2007 | Bigg et al. |
| 9,187,413 B2 | 11/2015 | Piomelli et al. |
| 2002/0173550 A1 | 11/2002 | Calignano et al. |
| 2003/0134894 A1 | 7/2003 | Piomelli et al. |
| 2003/0149082 A1 | 8/2003 | Makriyannis et al. |
| 2004/0048907 A1 | 3/2004 | Aquila et al. |
| 2004/0127518 A1 | 7/2004 | Piomelli et al. |
| 2007/0155707 A1 | 7/2007 | Dasse et al. |
| 2009/0048337 A1* | 2/2009 | Piomelli .............. C07C 271/56 514/484 |

(Continued)

FOREIGN PATENT DOCUMENTS

| | | |
|---|---|---|
| CN | 1671701 A | 9/2005 |
| CN | 1729171 A | 2/2006 |
| CN | 1741990 A | 3/2006 |

(Continued)

OTHER PUBLICATIONS

Agarwal, N. et al. (2007). "Cannabinoids mediate analgesia largely via peripheral type 1 cannabinoid receptors in nociceptors" *Nat. Neurosci* 10 (7), 870-879.
Ahn, K. et al. Novel Mechanistic Class of Fatty Acid Amide Hydrolase Inhibitors with Remarkable Selectivity. Biochemistry. 2007, vol. 46, pp. 13019-13030.
Alexander, J.P. et al. (2005). "Mechanism of carbamate inactivation of FAAH: implications for the design of covalent inhibitors and in vivo functional probes for enzymes," *Chem Biol* 12 (11), 1179-1187.

(Continued)

*Primary Examiner* — Joseph Kosack
(74) *Attorney, Agent, or Firm* — Zachary L. Terranova; Mintz, Levin, Cohn, Ferris, Glovsky and Popeo, P.C.

(57) ABSTRACT

The present invention provides methods of making and using peripherally restricted inhibitors of fatty acid amide hydrolase (FAAH). The present invention provides compounds and compositions that suppress FAAH activity and increases anandamide levels outside the central nervous system (CNS). The present invention also sets forth methods for inhibiting FAAH as well as methods for treating conditions such as, but not limited to, pain, inflammation, immune disorders, dermatitis, mucositis, the over reactivity of peripheral sensory neurons, neurodermatitis, and an overactive bladder. Accordingly, the invention also provides compounds, methods, and pharmaceutical compositions for treating conditions in which the selective inhibition of peripheral FAAH (as opposed to CNS FAAH) would be of benefit.

20 Claims, 3 Drawing Sheets

(56) References Cited

U.S. PATENT DOCUMENTS

| | | | |
|---|---|---|---|
| 2014/0163034 A1 | 6/2014 | Piomelli et al. |
| 2017/0088510 A1 | 3/2017 | Piomelli et al. |

FOREIGN PATENT DOCUMENTS

| | | |
|---|---|---|
| CN | 1922162 A | 2/2007 |
| JP | 2006/511484 | 4/2006 |
| WO | WO-98/20119 A1 | 5/1998 |
| WO | WO-03/097573 | 11/2003 |
| WO | WO-2004/033422 A2 | 4/2004 |
| WO | WO-2004/033422 A3 | 4/2004 |
| WO | WO-2008/063714 A1 | 5/2008 |
| WO | WO-2008/067196 A2 | 6/2008 |
| WO | WO-2008/067196 A3 | 6/2008 |
| WO | WO-2009/109504 A1 | 9/2009 |
| WO | WO-2011/046954 A1 | 4/2011 |
| WO | WO-2012/015704 A2 | 2/2012 |
| WO | WO-2012/015704 A3 | 2/2012 |
| WO | WO-2012/167133 A2 | 12/2012 |
| WO | WO-2012/167133 A3 | 12/2012 |
| WO | WO-2013/028570 A2 | 2/2013 |
| WO | WO-2013/028570 A3 | 2/2013 |
| WO | WO-2015/157313 A1 | 10/2015 |

OTHER PUBLICATIONS

Anand, P. et al. (2009). "Targeting CB2 receptors and the endocannabinoid system for the treatment of pain," *Brain Res Rev* 60(1):255-266.

Beltramo, M. et al. (Feb. 24, 1997). "Inhibition of anandamide hydrolysis in rat brain tissue by (E)-6-(bromomethylene) tetrahydro-3-(1-naphthalenyl)-2H-pyran-2-one," *FEBS Lett.* 403(3):263-267.

Bennett, G.J. et al. (1988). "A peripheral mononeuropathy in rat that produces disorders of pain sensation like those seen in man," *Pain* 33(1):87-107.

Bisogno, T., et al. (2002). "Fatty acid amide hydrolase, an enzyme with many bioactive substrates. Possible therapeutic implications," *Curr. Pharm. Des.* 8(7):533-547.

Boger, D. L. et al. (2005). *J Med Chem*, 48, 1849-1856.

Calignano, A. et al. (1998). "Control of pain initiation by endogenous cannabinoids," *Nature* 394 (6690):277-281.

Calignano, A et al. (2001). "Antinociceptive activity of the endogenous fatty acid amide, palmitylethanolamide," *Eur J Pharmacol* 419 (2-3), 191-198.

Casarotto, P.C. et al. (2016). "Unbound Medline: Cannabidiol Inhibitory Effect on Marble-Burying Behaviour: Involvmenet of CB1 Receptors," located at http://www.unboundmedicine.com/medline/citation/20695034/Cannabidiol_inhibitory_effect_on_marble_burying_behaviour:_involvmenet_of_CB1_receptors, last accessed May 17, 2016, abstract only, 2 pages.

Cee, V. et al. (2000). Journal of Medicinal Chemistry 53: 6368-6377.

Chaperon, F., et al. 1993). "Behavioral effects of cannabinoid agents in animals," *Crit. Rev. Neurobiol*, 13(3):243-281, abstract only.

Cippitelli, et al. Eur J Neurosci 26(2) pp. 476-86 (2007), abstract only.

Clapper, J.R. et al. (2009). "A second generation of carbamate-based fatty acid amide hydrolase inhibitors with improved activity in vivo," *ChemMedChem* 4(9):1505-1513.

Clapper, J.R. et al. (Oct. 2010, e-published Sep. 19, 2010). ""Anandamide suppresses pain initiation through a peripheral endocannabinoid mechanism,"" Nat. Neurosci 13(10):1265-1270.

Cravatt, B.F. et al. (1996). "Molecular characterization of an enzyme that degrades neuromodulatory fatty-acid amides," *Nature*, 384(6604):83-87.

Cravatt, B.F. et al. (2001). "Supersensitivity to anandamide and enhanced endogenous cannabinoid signaling in mice lacking fatty acid amide hydrolase," *Proc Natl Acad Sci USA* 98(16):9371-9376.

Cravatt, B.F. et al. (2004). "Functional disassociation of the central and peripheral fatty acid amide signaling systems," *Proc Natl Acad Sci USA* 101(29):10821-10826.

Del Arco et al., Eur J Pharmacol 454(1) pp. 103-104 (2003).

Deutsch, D.G., et al. (Feb.-Mar. 2002). "The fatty acid amide hydrolase (FAAH)," *Prostaglandins Leukot. Essent. Fatty Acid* 66(2-3):201-210.

Devane, W.A. et al. (1992). "Isolation and structure of a brain constituent that binds to the cannabinoid receptor. *Science*," 258(5090):1946-1949, abstract only.

Di Marzo, V. et al. (Dec. 15, 1994). "Formation and inactivation of endogenous cannabinoid anandamide in central neurons," *Nature*, 372:686-691.

Dinh, T.P., et al. (Aug. 6, 2002, e-published Jul. 22, 2002). "Brain monoglyceride lipase participating in endocannabinoid inactivation," *Proc. Natl. Acad. Sci. U.S.A.* 99(16):10819-10824.

Duncton, M.A.J. et al. (2009). "Arylphthalazines as potent, and orally bioavailable inhibitors of VEGFR-2," *Bioorganic & Medicinal Chemistry* 17(2):731-740.

Dziadulewicz, E.K. et al. (2007). "Naphthalen-1-yl-(4-pentyloxynaphthalen-1-yl)methanone: a potent, orally bioavailable human CB1/CB2 dual agonist with antihyperalgesic properties and restricted central nervous system penetration," *J Med Chem* 50(16): 3851-3856.

Fegley, D. et al. (2005). "Characterization of the fatty acid amide hydrolase inhibitor cyclohexyl carbamic acid 3'-carbamoyl-biphenyl-3-yl ester (URB597): effects on anandamide and oleoylethanolamide deactivation," *J Pharmacol Exp Ther* 313(1):352-358.

Forster, L. et al. (Jan. 15, 2010, e-published Nov. 17, 2009). "1-Indol-1-yl-propan-2-ones and related heterocyclic compounds as dual inhibitors of cytosolic phospholipase A(2)alpha and fatty acid amide hydrolase," *Bioorg Med Chem* 18(2):945-952.

Fowler, C. J., et al. (Sep. 1, 2001). "Fatty acid amide hydrolase: biochemistry, pharmacology, and therapeutic possibilities for an enzyme hydrolyzing anandamide, 2-arachidonoylglycerol, palmitoylethanolamide, and oleamide," *Biochem. Pharmacol.* 62(5):517-526.

Fu, J. et al., J Biol Chem, 282(2):1518-1528. (2007).

Fu, J. et al., "A catalytically silent FAAH-1 variant drives anandamide transport in neurons", Nat. Neurosci., Nov. 20, 2011, vol. 15, No. 1, pp. 64-69.

Giuffrida, A. et al., Eur J Pharmacol, 408 161-168 (2000).

Glaser, S. T. et al., Proc Natl Acad Sci USA, 100(7):4269-4274. (2003).

Gomes et al. Prog Neuropsychopharmacol Biol Psychiatry. 35:434-438 (2011).

Guindon, J. et al. (2008). "Cannabinoid CB2 receptors: a therapeutic target for the treatment of inflammatory and neuropathic pain," *Br J Pharmacol* 153(2):319-334.

Hall, W., et al. (Nov. 14, 1998). "Adverse effects of cannabis," *Lancet*, 352(9140):1611-1616.

Hillard, C. J. et al., J Mol Neurosci, 33(1):18-24 (2007).

Hohmann, A.G. et al. (1999). "Localization of central cannabinoid CB1 receptor messenger RNA in Neuronal subpopulations of rat dorsal root ganglia: a double-label in situ hybridization study," *Neuroscience* 90(3):923-931.

Hohmann, A.G. et al. (1999). "Cannabinoid receptors undergo axonal flow in sensory nerves," *Neuroscience* 92(4):1171-1175.

International Preliminary Report on Patentability dated Dec. 2, 2013 for International Application No. PCT/US2012/040531, 6 pages.

International Search Report and Written Opinion dated Mar. 22, 2013 for International Application No. PCT/US2012/040531, 9 pages.

International Search Report corresponding to the PCT/US2011/045114 application, mailed Apr. 6, 2012, 4 pages.

International Search Report mailed on Feb. 18, 2013, for PCT Application No. PCT/US2012/051478, filed Aug. 17, 2012, 4 pages.

Jaggar, S.I. et al. (1998). "The endogenous cannabinoid anandamide, but not the CB2 ligand palmitoylethanolamide, prevents the viscero-visceral hyper-reflexia associated with inflammation of the rat urinary bladder," *Neurosci Lett* 253(2):123-126.

(56) References Cited

OTHER PUBLICATIONS

Kathuria, S. et al. (Jan. 2003, e-published Dec. 2, 2002). "Modulation of anxiety through blockade of anandamide hydrolysis," *Nat Med* 9(1):76-81.
Kaufmann, I. et al. (2009). "Enhanced anandamide plasma levels in patients with complex regional pain syndrome following traumatic injury: a preliminary report," *Eur Surg Res* 43(4):325-329 (2009).
Lambert, D.M., et al. (Mar. 2002). "The palmitoylethanolamide family: a new class of anti-inflammatory agents?" *Curr. Med. Chem.* 9(6): 663-674, abstract only.
Lever, I. J. et al. (2009). "Localization of the endocannabinoid-degrading enzyme fatty acid amide hydrolase in rat dorsal root ganglion cells and its regulation after peripheral nerve injury," *J Neurosci* 29(12): 3766-3780.
Loscher, W. et al. (2005). "Blood-brain barrier active efflux transporters: ATP-binding cassette gene family," *NeuroRx* 2(1):86-98.
LoVerme, J. et al. (2005). "The search for the palmitoylethanolamide receptor," *Life Sci* 77(14):1685-1698.
LoVerme, J. et al. (2006). "Rapid broad-spectrum analgesia through activation of peroxisome proliferator-activated receptor-alpha," *J Pharmacol Exp Ther* 319(3):1051-1061.
Mackie, K. (2006). "Cannabinoid receptors as therapeutic targets," *Annu Rev Pharmacol Toxicol* 46:101-122.
McKinney, M. K. et al., Annu Rev Biochem, 74, 411-432 (2005).
Mileni, M. et al., J Mol Biol, 400(4):743-754 (2010).
Mitrirattanakul, S. et al. (2006). "Site-specific increases in peripheral cannabinoid receptors and their endogenous ligands in a model of neuropathic pain," *Pain* 126(1-3): 102-114.
Mor, M. et al. 'Cyclohexylcarbamic Acid 3- or 4-Substituted Biphenyl-3-yl Esters as Fatty Acid Amide Hydrolase Inhibitors:Synthesis, Quantitative Structure-Activity Relationships,and Molecular Modeling Studies.' J. Med.Chem. 2004, vol. 47, pp. 4998-5008.
Moreno-Sanz, G. et al. (Oct. 2011, e-published Jul. 7, 2011). "The ABC membrane transporter ABCG2 prevents access of FAAH inhibitor URB937 to the central nervous system," Pharmacol Res 64(4):359-363.
Nackley, A.G. et al. (2003). "A peripheral cannabinoid mechanism suppresses spinal fos protein expression and pain behavior in a rat model of inflammation," *Neuroscience* 117(3), 659-670.
Niforatos, Wende et al. "Activation of TRPA1 Channels by the Fatty Acid Amide Hydrolase Inhibitor 3-Carbamoylbiphenyl-3-yl cyclohexylcarbamate (URB597)," Mol. Pharmacol. 2007, vol. 71, pp. 1209-1216.
Ortega-Gutierrez, S. et al. (2004). *Biochemistry*, 43:8184-8190.
Patricelli, M.P. et al. (1999). "Chemical and mutagenic investigations of fatty acid amide hydrolase: evidence for a family of serine hydrolases with distinct catalytic properties," *Biochemistry*, 38:9804-9812.
Patricelli, M. P. et al. (1999). *Biochemistry* 38:14125-14130.
Piatnitski, E.L. et al. (Nov. 1, 2005). "Arylphthalazines: identification of a new phthalazine chemotype as inhibitors of VEGFR kinase," *Bioorg Med Chem Lett* 15(21):4696-4698.
Piomelli, D. et al. (May 1999). *Proc Natl Acad Sci USA* 96:5802-5807.
Piomelli, D., et al. (Jun. 2000). "The endocannabinoid system as a target for therapeutic drugs," *Trends Pharmacol. Sci.* 21(6):218-224.
Piomelli, D. et al. (2006). Pharmacological profile of the selective FAAH inhibitor KDS-4103 (URB597). *CNS Drug Rev* 12(1):21-38.
PubChem Compound ID 5514389 [http://pubchem.ncbi.nlm.nih.gov/summary/summary.cgi?q=all&cid=5514389] Retrieved from the Internet on Aug. 20, 2014, 13 pages.
Puig, S. et al. (1996). "Formalin-evoked activity in identified primary afferent fibers: systemic lidocaine suppresses phase-2 activity," *Pain* 64(2): 345-355.
Richardson, J.D. et al. (1998). "Cannabinoids reduce hyperalgesia and inflammation via interaction with peripheral CB1 receptors," *Pain* 75(1):111-119.

Richardson, D. et al. (2008, e-published Apr. 16, 2008). "Characterisation of the cannabinoid receptor system in synovial tissue and fluid in patients with osteoarthritis and rheumatoid arthritis," *Arthritis Res Ther* 10(2):R43.
Russo, R. et al., The fatty acid amide hydrolase inhibitor URB597(cyclohexylcarbamic acid 3'-carbamoylbiphenyl-3-ylester) reduces neuropathic pain after oral administration in mice. J Pharmacol Exp Ther 322(1):236-242 (2007).
Sagar, D.R. et al. (2008). "Inhibition of fatty acid amide hydrolase produces PPAR-alpha-mediated analgesia in a rat model of inflammatory pain," *Br J Pharmacol* 155(8): 1297-1306.
Scherma, M. (2012). Br J Pharmacol 165:2539-2548.
Schlosburg, J.E. et al. (2009). "Targeting fatty acid amide hydrolase (FAAH) to treat pain and inflammation," *AAPS J* 11(1):39-44.
Seierstad, M. et al. (Dec. 11, 2008). *J Med Chem*, 51(23):7327-7343.
Starowicz, K. et al. (2007). "Biochemistry and pharmacology of endovanilloids," *Pharmacol Ther* 114(1):13-33.
Stein, C. et al. (2003). "Attacking pain at its source: new perspectives on opioids," *Nat Med* 9(8):1003-1008.
Stein, C. et al. (2009). "Opioids and sensory nerves," *Handb Exp Pharmacol* (194):495-518.
Tegeder, I. et al. (2003). "Peripheral opioid analgesia in experimental human pain models," *Brain* 126(Pt 5):1092-1102.
Vacondio, F. et al. (Sep. 2009). "Structure-property relationships of a class of carbamate-based fatty acid amide hydrolase (FAAH) inhibitors: chemical and biological stability," *ChemMedChem* 4(9):1495-1504.
Wei, B. Q. et al. (2006). J Biol Chem, 281(48): 36569-36578.
Wendeler, M. et al. (Jul. 7, 2003). "Inhibitors of endocannabinoid degradation: potential therapeutics for neurological disorders," *Angew. Chem. Int. Ed.* 42(26):2938-2941.
Written Opinion mailed on Feb. 18, 2013, for PCT Application No. PCT/US2012/051478, filed Aug. 17, 2012, 6 pages.
U.S. Appl. No. 60/336,289, filed Oct. 31, 2001.
U.S. Appl. No. 61/492,293, filed Jun. 1, 2011.
U.S. Appl. No. 61/368,500, filed Jul. 28, 2010.
Ahn, K. et al. (May 2008, e-published Apr. 23, 2008). "Enzymatic pathways that regulate endocannabinoid signaling in the nervous system," *Chem Rev* 108(5):1687-1707.
Beltramo, M. et al. (Aug. 22, 1997). "Functional role of high-affinity anandamide transport, as revealed by selective inhibition," *Science* 277(5329):1094-1097.
Boger, D.L. et al. (Aug. 1998). "Oleamide: an endogenous sleep-inducing lipid and prototypical member of a new class of biological signaling molecules," *Curr Pharm Des* 4(4):303-314.
Chaperon, F. et al. (1999). "Behavioral effects of cannabinoid agents in animals," *Crit Rev Neurobiol* 13(3):243-281.
Cravatt, B.F. et al. (Aug. 2003). "Fatty acid amide hydrolase: an emerging therapeutic target in the endocannabinoid system," *Curr Opin Chem Biol* 7(4):469-475.
Di Marzo, V. et al. (Apr. 2007). "Endocannabinoids and the regulation of their levels in health and disease," *Curr Opin Lipidol* 18(2):129-140.
Di Marzo, V. et al. (May 2008). "Targeting the endocannabinoid system: to enhance or reduce?" *Nat Rev Drug Discov* 7(5):438-455.
Eckert, H. et al. (1987). "Triphogene, a Crystalline Phosgene Substitute," *Angew Chem Int Ed Engl* 26(9):894-895.
Fowler, C.J. (Jan. 2004, e-published Dec. 22, 2003). "Oleamide: a member of the endocannabinoid family?" *Br J Pharmacol* 141(2):195-196.
Fu, J.et al. (Sep. 4, 2003). "Oleylethanolamide regulates feeding and body weight through activation of the nuclear receptor PPAR-alpha," *Nature* 425(6953):90-93.
Hansen, H.S. et al. (Jul. 2010, e-publsihed Mar. 29, 2010). "Palmitoylethanolamide and other anandamide congeners. Proposed role in the diseased brain," *Exp Neurol* 224(1):48-55.
Kotha, S. et al. (2002). "Recent applications of the Suzuki-Miyaura cross-coupling reaction in organic synthesis," *Tetrahedron* 58:9633-9695.
Lambert, D.M. et al. (Mar. 2002). "The palmitoylethanolamide family: a new class of anti-inflammatory agents?" *Curr Med Chem* 9(6):663-674.

(56) References Cited

OTHER PUBLICATIONS

Lambert, D.M. et al. (Nov. 2007). "Endocannabinoids and related N-acylethanolamines in the control of appetite and energy metabolism: emergence of new molecular players," *Curr Opin Clin Nutr Metab Care* 10(6):735-744.
Lange, J.H. et al.(Mar. 24, 2005). "Bioisosteric replacements of the pyrazole moiety of rimonabant: synthesis, biological properties, and molecular modeling investigations of thiazoles, triazoles, and imidazoles as potent and selective CB1 cannabinoid receptor antagonists," *J Med Chem* 48(6):1823-1838.
Lima, L.M. et al. (2005). "Bioisosterism: a useful strategy for molecular modification and drug design," *Curr Med Chem* 12(1):23-49.
Miyaura, N. et al. (1995). "Palladium-Catalyzed Cross-Coupling Reactions of Organoboron Compounds," *Chem Rev* 95:2457-2483.
Muccioli, G.G. (Jun. 2010, e-published Mar. 19, 2010). "Endocannabinoid biosynthesis and inactivation, from simple to complex," *Drug Discov Today* 15(11-12):474-483.
Patricelli, M.P. et al. (2001). "Proteins regulating the biosynthesis and inactivation of neuromodulatory fatty acid amides," *Vitam Horm* 62:95-131.
Piomelli, D. et al. (Jul. 2005). "The endocannabinoid system: a drug discovery perspective," *Curr Opin Investig Drugs* 6(7):672-679.
Piomelli, D. (Jul. 2013, e-published Apr. 6, 2013). "A fatty gut feeling," *Trends Endocrinol Metab* 24(7):332-341.
PubChem. Compound Summary for: CID 11773226. Create Date: Oct. 27, 2006. [last accessed Dec. 28, 2016]. located at <https://pubchem.ncbi.nlm.nih.gov/summary/summary.cgi?cid=11773226>, 13 pages.
PubChem. Compound Summary for: CID 71506770. Create Date: Jun. 10, 2013. [last accessed Dec. 28, 2016]. located at <https://pubchem.ncbi.nlm.nih.gov/compund/71506770>, 13 pages.
PubChem. Substance Record for SID 174502363. Available Date: Apr. 3, 2014 [last accessed on Dec. 28, 2016]. located at <https://pubchem.ncbi.nlm.nih.gov/substance/174502363>, 7 pages.
Schwartz, G.J. et al. (Oct. 2008). "The lipid messenger OEA links dietary fat intake to satiety," *Cell Metab* 8(4):281-288.
Suzuki, A. (Jul. 18, 2011, e-published May 25, 2011). "Cross-coupling reactions of organoboranes: an easy way to construct C-C bonds (Nobel Lecture)," *Angew Chem Int Ed Engl* 50(30):6722-6737.
Ueda, N. et al. (Oct. 2010, e-published Feb. 10, 2010). "N-acylethanolamine metabolism with special reference to N-acylethanolamine-hydrolyzing acid amidase (NAAA)," *Prog Lipid Res* 49(4):299-315.
Astarita, G. et al. (Jan. 2008, e-published Oct. 23, 2007). Identification of biosynthetic precursors for the endocannabinoid anandamide in the rat brain. *J Lipid Res* 49(1):48-57.
Beltramo, M. et al. (Apr. 27, 2000). "Carrier-mediated transport and enzymatic hydrolysis of the endogenous cannabinoid 2-arachidonylglycerol," *Neuroreport*, 11(6):1231-1235.
Beltramo, M. et al. (May 2000). "Reversal of dopamine D(2) receptor responses by an anandamide transport inhibitor,"*J Neurosci* 20(9):3401-3407.
Cadas, H. et al. (Feb. 15, 1997). Occurrence and biosynthesis of endogenous cannabinoid precursor, N-arachidonoyl phosphatidylethanolamine, in rat brain. *J Neurosci* 17 (4):1226-1242.
Glaucoma (Jun. 2, 2017). retrieved from http://www.mayoclinic.org/diseases-conditions/glaucoma/basics/prevention/con-20024042> last visited Jun. 2, 2017, 5 pages.
Gomes, P.B. et al. (Sep. 2010, e-published May 31, 2010). "Anxiolytic-like effect of the monoterpene 1,4-cineole in mice," *Pharmacol Biochem Behav* 96(3):287-293.
Kotha, S. et al. (2002). "Recent applications of the Suzuki-Miyaura cross-coupling reaction in organic synthetis," *Tetrahedron* 58:9633-9695.
Tarzia, G. et al. (Jan. 2006). "Synthesis and structure-activity relationships of FAAH inhibitors: cyclohexylcarbamic acid biphenyl esters with chemical modulation at the proximal phenyl ring," ChemMedChem 1(1):130-139.
Casarotto, P.C. et al. (Jul. 2010). "Cannabidiol inhibitory effect on marble-burying behaviour: involvement of CB1 receptors," *Behav Pharmacol* 21(4):353-358.

\* cited by examiner

META-SUBSTITUTED BIPHENYL PERIPHERALLY RESTRICTED FAAH INHIBITORS

CROSS-REFERENCES TO RELATED APPLICATIONS

This application is a continuation application of PCT Application No. PCT/US2012/051478 filed Aug. 17, 2012, which claims priority to, and the benefit of, U.S. Provisional application Ser. No. 61/525,636 filed Aug. 19, 2011, the disclosure of which is incorporated herein by reference in its entirety.

STATEMENT AS TO RIGHTS TO INVENTIONS MADE UNDER FEDERALLY SPONSORED RESEARCH AND DEVELOPMENT

This invention was made with Government support under NIH Grant No. R01 DA012413 and NIDA Grant Nos. R01 DA012447 and RL1 AA017538 awarded by the National Institutes of Health. The U.S. Government has certain rights in this invention.

BACKGROUND OF THE INVENTION

Anandamide, the naturally occurring amide of arachidonic acid with ethanolamine, meets all key criteria of an endogenous cannabinoid substance (Devane, W. A. et al. *Science*, 258, 1946-1949 (1992)): it is released upon demand by stimulated neurons (Di Marzo, V. et al., *Nature*, 372, 686-691 (1994); Giuffrida, A. et al., *Nat. Neurosci.*, 2, 358-363 (1999)); it activates cannabinoid receptors with high affinity (Devane, W. A. et al. *Science*, 258, 1946-1949 (1992)) and it is rapidly eliminated through a two-step process consisting of carrier-mediated transport followed by intracellular hydrolysis (Di Marzo, V. et al., *Nature*, 372, 686-691 (1994); Beltramo, M. et al., *FEBS Lett.*, 403, 263-267 (1997)). Anandamide hydrolysis is catalyzed by the enzyme fatty acid amide hydrolase (FAAH), a membrane-bound serine hydrolase (Cravatt, B. F. et al., *Nature*, 384, 83-87 (1996); Patricelli, M. P. et al., *Biochemistry*, 38, 9804-9812 (1999)) (WO 98/20119) (U.S. Pat. No. 6,271,015) that also cleaves other bioactive fatty ethanolamides, such as oleoylethanolamide (cis-9-octadecenamide)) (Rodríguez de Fonseca, F. et al. *Nature*, 414, 209-212 (2001)) and palmitoylethanolamide (Calignano, A. et al., *Nature*, 394, 277-281 (1998)). Mutant mice lacking the gene encoding for FAAH cannot metabolize anandamide (Cravatt, B. F. et al., *Proc. Natl. Acad. Sci. U.S.A.*, 98, 9371-9376 (2001)) and, though fertile and generally normal, show signs of enhanced anandamide activity at cannabinoid receptors, such as reduced pain sensation (Cravatt, B. F. et al., *Proc. Natl. Acad. Sci. U.S.A.*, 98, 9371-9376 (2001)). This suggests the possibility that drugs targeting FAAH may heighten the tonic actions of anandamide, while possibly avoiding the multiple, often unwanted effects produced by $\Delta^9$-THC and other direct-acting cannabinoid agonists (Hall, W., et al., *Lancet*, 352, 1611-1616 (1998); Chaperon, F., et al., *Crit. Rev. Neurobiol.*, 13, 243-281 (1999)).

Pain perception can be effectively controlled by neurotransmitters that operate within the CNS. This modulation has been well characterized in the dorsal horn of the spinal cord, where impulses carried by nociceptive (pain-sensing) fibers are processed before they are transmitted to the brain. In addition to these central mechanisms, intrinsic control of pain transmission can occur at terminals of afferent nerve fibers outside the CNS. One prominent example of peripheral regulation is provided by the endogenous opioids, which are released from activated immune cells during inflammation and inhibit pain initiation by interacting with opioid receptors localized on sensory nerve endings[1,2].

It has been proposed that endocannabinoid mediators might serve an analogous function to that of the opioids, because pharmacological activation of peripheral $CB_1$ and $CB_2$ cannabinoid receptors inhibits pain-related behaviors[3-7] while genetic disruption of $CB_1$ receptor expression in primary nociceptive neurons exacerbates such behaviors[8]. Moreover, there is evidence that clinical conditions associated with neuropathic pain or inflammation, such as complex regional pain syndrome and arthritis, may be accompanied by peripheral elevations in the levels of the endocannabinoid anandamide[9,10]. Another major endocannabinoid ligand, 2-arachidonoylglycerol (2-AG), has also been implicated in nociceptive signaling outside the CNS[8,11].

Much attention has been directed toward the role of anandamide in pain. Methods of treating pain by administering anandamide and palmitoylethanolamide are disclosed in U.S. Patent Application Publication No.: 20020173550. Methods of treating pain by administering inhibitors of FAAH are disclosed in U.S. Patent Application Publication Nos. 20040127518 and 20030134894. Methods of treating pain by administering inhibitors of anandamide transport are disclosed in U.S. Patent Application Publication No. 20030149082.

Although these findings suggest that the endocannabinoid system serves an important function in the peripheral regulation of nociception, they offer no definitive insight on the identity of the endogenous ligand, or ligands, involved in this function. Thus there exists a need related to an understanding, at a molecular level, of the intrinsic mechanisms that control pain initiation in order to identify new analgesic agents devoid of central side effects. Surprisingly, the present invention satisfies this as well as many other needs by identifying, characterizing, and making brain-impermeant inhibitors of the anandamide-degrading enzyme, FAAH, with the aim of magnifying the actions of peripheral anandamide and unmasking their possible role in the control of emerging pain signals[12]. Another need in the field of developing and therapeutically using FAAH inhibitors is related to the ability of these inhibitors to modulate endogenous cannabinoid systems within the CNS system to cause unwanted psychotropic or mood-altering effects. The present invention also surprisingly satisfies these and other needs by providing peripherally restricted FAAH inhibitors and methods of their use in the treatment of a variety of conditions, including pain and/or inflammation.

The following references may provide background information for the field to which the present invention pertains. The disclosure of each reference is hereby incorporated by reference in its entirety for all purposes. (1) Stein, C., Schafer, M., & Machelska, H., Attacking pain at its source: new perspectives on opioids. Nat Med 9 (8), 1003-1008 (2003); 2) Stein, C. & Zollner, C., Opioids and sensory nerves. Handb Exp Pharmacol (194), 495-518 (2009); 3) Calignano, A., La Rana, G., Giuffrida, A., & Piomelli, D., Control of pain initiation by endogenous cannabinoids. Nature 394 (6690), 277-281 (1998); 4) Jaggar, S. I., Sellaturay, S., & Rice, A. S., The endogenous cannabinoid anandamide, but not the CB2 ligand palmitoylethanolamide, prevents the viscero-visceral hyper-reflexia associated with inflammation of the rat urinary bladder. Neurosci Lett 253 (2), 123-126 (1998); 5) Nackley, A. G., Suplita, R. L., 2nd, & Hohmann, A. G., A peripheral cannabinoid mechanism suppresses spinal fos protein expression and pain behavior in a rat model of inflammation. Neuroscience 117 (3), 659-670 (2003); 6) Dziadulewicz, E. K. et al., Naphthalen-1-yl-(4-pentyloxynaphthalen-1-yl)methanone: a potent, orally bioavailable human CB1/CB2 dual agonist with anti-hyperalgesic properties and restricted central nervous system penetration. J Med Chem 50 (16), 3851-3856 (2007); 7) Anand, P., Whiteside, G., Fowler, C. J., & Hohmann, A. G., Targeting CB2 receptors and the endocannabinoid system for the treatment of pain. Brain Res Rev 60 (1), 255-266 (2009); 8) Agarwal, N. et al., Cannabinoids mediate analgesia largely via peripheral type 1 cannabinoid receptors in nociceptors. Nat Neurosci 10 (7), 870-879 (2007); 9) Kaufmann, I. et al., Enhanced anandamide plasma levels in patients with complex regional pain syndrome following traumatic injury: a preliminary report. Eur Surg Res 43 (4), 325-329 (2009); 10) Richardson, D. et al., Characterisation of the cannabinoid receptor system in synovial tissue and fluid in patients with osteoarthritis and rheumatoid arthritis. Arthritis Res Ther 10 (2), R43 (2008) 11) Mitrirattanakul, S. et al., Site-specific increases in peripheral cannabinoid receptors and their endogenous ligands in a model of neuropathic pain. Pain 126 (1-3), 102-114 (2006); 12)

Schlosburg, J. E., Kinsey, S. G., & Lichtman, A. H., Targeting fatty acid amide hydrolase (FAAH) to treat pain and inflammation. AAPS J 11 (1), 39-44 (2009); 13) Kathuria, S. et al., Modulation of anxiety through blockade of anandamide hydrolysis. Nat Med 9 (1), 76-81 (2003); 14) Piomelli, D. et al., Pharmacological profile of the selective FAAH inhibitor KDS-4103 (URB597). CNS Drug Rev 12 (1), 21-38 (2006); 15 Clapper, J. R. et al., A second generation of carbamate-based fatty acid amide hydrolase inhibitors with improved activity in vivo. ChemMedChem 4 (9), 1505-1513 (2009); 16) Alexander, J. P. & Cravatt, B. F., Mechanism of carbamate inactivation of FAAH: implications for the design of covalent inhibitors and in vivo functional probes for enzymes. Chem Biol 12 (11), 1179-1187 (2005); 17) Loscher, W. & Potschka, H., Blood-brain barrier active efflux transporters: ATP-binding cassette gene family. NeuroRx 2 (1), 86-98 (2005); 18) Cravatt, B. F. et al., Supersensitivity to anandamide and enhanced endogenous cannabinoid signaling in mice lacking fatty acid amide hydrolase. Proc Natl Acad Sci USA 98 (16), 9371-9376 (2001); 19) Starowicz, K., Nigam, S., & Di Marzo, V., Biochemistry and pharmacology of endovanilloids. Pharmacol Ther 114 (1), 13-33 (2007); 20) LoVerme, J., La Rana, G., Russo, R., Calignano, A., & Piomelli, D., The search for the palmitoylethanolamide receptor. Life Sci 77 (14), 1685-1698 (2005); 21) Sagar, D. R., Kendall, D. A., & Chapman, V., Inhibition of fatty acid amide hydrolase produces PPAR-alpha-mediated analgesia in a rat model of inflammatory pain. Br J Pharmacol 155 (8), 1297-1306 (2008); 22) Coderre, T. J. & Melzack, R., The contribution of excitatory amino acids to central sensitization and persistent nociception after formalin-induced tissue injury. J Neurosci 12 (9), 3665-3670 (1992); 23) Puig, S. & Sorkin, L. S., Formalin-evoked activity in identified primary afferent fibers: systemic lidocaine suppresses phase-2 activity. Pain 64 (2), 345-355 (1996); 24) Bennett, G. J. & Xie, Y. K., A peripheral mononeuropathy in rat that produces disorders of pain sensation like those seen in man. Pain 33 (1), 87-107 (1988); 25) Ahluwalia, J., Yaqoob, M., Urban, L., Bevan, S., & Nagy, I., Activation of capsaicin-sensitive primary sensory neurones induces anandamide production and release. J Neurochem 84 (3), 585-591 (2003); 26) Liu, J. et al., A biosynthetic pathway for anandamide. Proc Natl Acad Sci USA 103 (36), 13345-13350 (2006); 27) Hohmann, A. G. & Herkenham, M., Localization of central cannabinoid CB1 receptor messenger RNA in neuronal subpopulations of rat dorsal root ganglia: a double-label in situ hybridization study. Neuroscience 90 (3), 923-931 (1999); 28) Hohmann, A. G. & Herkenham, M., Cannabinoid receptors undergo axonal flow in sensory nerves. Neuroscience 92 (4), 1171-1175 (1999); 29) Richardson, J. D., Kilo, S., & Hargreaves, K. M., Cannabinoids reduce hyperalgesia and inflammation via interaction with peripheral CB1 receptors. Pain 75 (1), 111-119 (1998); 30) Mackie, K., Cannabinoid receptors as therapeutic targets. Annu Rev Pharmacol Toxicol 46, 101-122 (2006); 31) LoVerme, J. et al., Rapid broad-spectrum analgesia through activation of peroxisome proliferator-activated receptor-alpha. J Pharmacol Exp Ther 319 (3), 1051-1061 (2006); 32) Guindon, J. & Hohmann, A. G., Cannabinoid CB2 receptors: a therapeutic target for the treatment of inflammatory and neuropathic pain. Br J Pharmacol 153 (2), 319-334 (2008); 33) Cravat, B. F. et al., Functional disassociation of the central and peripheral fatty acid amide signaling systems. Proc Natl Acad Sci USA 101 (29), 10821-10826 (2004); 34) Lever, I. J. et al., Localization of the endocannabinoid-degrading enzyme fatty acid amide hydrolase in rat dorsal root ganglion cells and its regulation after peripheral nerve injury. J Neurosci 29 (12), 3766-3780 (2009); 35) Tegeder, I. et al., Peripheral opioid analgesia in experimental human pain models. Brain 126 (Pt 5), 1092-1102 (2003); 36) King, A. R. et al., URB602 inhibits monoacylglycerol lipase and selectively blocks 2-arachidonoylglycerol degradation in intact brain slices. Chem Biol 14 (12), 1357-1365 (2007); 37) Astarita, G., Ahmed, F., & Piomelli, D., Identification of biosynthetic precursors for the endocannabinoid anandamide in the rat brain. J Lipid Res 49 (1), 48-57 (2008); 38) Fegley, D. et al., Characterization of the fatty acid amide hydrolase inhibitor cyclohexyl carbamic acid 3'-carbamoyl-biphenyl-3-yl ester (URB597): effects on anandamide and oleoylethanolamide deactivation. J Pharmacol Exp Ther 313 (1), 352-358 (2005); 39) Cadas, H., di Tomaso, E., & Piomelli, D., Occurrence and biosynthesis of endogenous cannabinoid precursor, N-arachidonoyl phosphatidylethanolamine, in rat brain. J Neurosci 17 (4), 1226-1242 (1997); 40) Hargreaves, K., Dubner, R., Brown, F., Flores, C., & Joris, J., A new and sensitive method for measuring thermal nociception in cutaneous hyperalgesia. Pain 32 (1), 77-88 (1988).

BRIEF SUMMARY OF THE INVENTION

In a first aspect, the invention provides compounds, and pharmaceutical compositions of the compounds, having Formula I:

Formula I

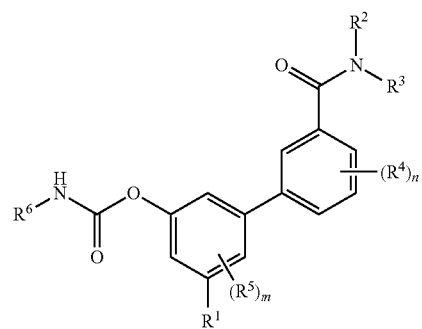

In Formula I, $R^1$ is selected from the group consisting of hydrogen, hydroxy and the physiologically hydrolyzable esters thereof, —SH, carboxy and the physiologically hydrolysable esters thereof, a hydroxy lower $(C_1$-$C_3)$alkyl (e.g., —$CH_2OH$, —$CH_2CH_2OH$, and —$CH(OH)CH_3$) and the physiologically hydrolyzable esters thereof, —$NR^7R^8$, and —$NHSO_2R^9$; wherein $R^7$ and $R^8$ are independently selected from hydrogen or unsubstituted $(C_1$-$C_3)$alkyl and $R^9$ is hydrogen, methyl, ethyl, trifluoromethyl or trifluoroethyl; $R^2$ and $R^3$ are independently hydrogen or substituted or unsubstituted $(C_1$-$C_3)$alkyl; each $R^4$ is independently hydrogen or substituted or unsubstituted $(C_1$-$C_3)$alkyl and n is an integer from 0 to 4; each $R^5$ is independently hydrogen, halogen, hydroxy and the physiologically hydrolyzable esters thereof, carboxy and the physiologically hydrolyzable esters thereof, hydroxyl-$(C_1$-$C_3)$alkyl and the physiologically hydrolyzable esters thereof, —$(C_1$-$C_3)$alkoxy, or —$NR^{20}R^{21}$; and $R^{20}$ and $R^{21}$ are independently selected from hydrogen or $(C_1$-$C_3)$ alkyl; m is an integer from 0 to 3; $R^6$ is a cyclohexyl, cyclopentyl, cyclobutyl or tetrahydropyran-4-yl which may be substituted or unsubstituted. Also included are the pharmaceutically acceptable salts thereof. In some embodiments, m and n are each 0, $R^2$ and $R^3$ are each H; and $R^1$ is hydroxy, carboxy, hydroxymethyl, or hydroxyethyl; and $R^6$ is cyclohexyl. In some embodiments, the cyclohexyl is substituted or unsubstituted. Also include are the physiologically acceptable esters thereof. The compounds set forth herein have the advantageous property of being peripherally restricted FAAH inhibitors with accordingly reduced potential for side-effects on the central nervous system.

In a second aspect, the invention provides pharmaceutical compositions comprising a therapeutically effective amount of the compounds according to the invention. The compositions can be formulated for any route of administration including the oral and parenteral routes. In addition, the compositions may be in a unit dose format.

In a third aspect, the invention provides a method of treating a subject in need of a peripherally restricted FAAH inhibitor (e.g., a FAAH inhibitory compound according to the invention). In preferred embodiments, the subject is a human. In some embodiments, the need is with respect to a treatment for pain, inflammation, or an immune disorder of the subject. In some embodiments, the pain can be nociceptive, inflammatory, or neuropathic pain. Preferably, the peripherally restricted FAAH inhibitory compound is a compound of the invention.

In a fourth aspect, the invention provides a method of enhancing the peripheral activity of an endogenously produced (i.e., an endocannabinoid such as anandamide, N-arachidonoyl dopamine) or exogenously provided cannabinoid fatty acid amide in a subject by administering a compound according to the invention. Preferably, the fatty acid amide is anandamide, N-arachidonoyl dopamine, oleoylethanolamide, stearoylethanolamide, or palmitoylethanolamide. Where the fatty ethanolamide is exogenously provided, the fatty acid ethanolamide can be administered to the subject before, after, or contemporaneous with the administration of the compound according to the invention. In some embodiments, the subject is in need of treatment for pain, inflammation, or an immune disorder. In preferred embodiments, the pain can be nociceptive, inflammatory, or neuropathic pain.

In a fifth aspect, the invention provides a pharmaceutical composition for treating a condition selected from dermatitis, mucositis, or the over reactivity of peripheral sensory neurons, neurodermatitis, overactive bladder, or cough wherein said composition comprises a compound according to the invention and a pharmaceutically acceptable excipient. In some embodiments of any of the above, the condition is a chemical, drug- or radiation-induced pathology. Accordingly, in this aspect the invention also provides methods of treating a condition selected from dermatitis, mucositis, or the over reactivity of peripheral sensory neurons, neurodermatitis, overactive bladder, or cough pain and/or inflammation by administering to a mammal in need thereof, a therapeutically effective amount of a compound according to the invention.

DETAILED DESCRIPTION OF THE INVENTION

1. General

The present invention provides methods of making and using peripherally restricted inhibitors of fatty acid amide hydrolase (FAAH). The present invention provides compounds that suppress FAAH activity and increases anandamide levels outside the central nervous system (CNS). Despite their relative inability to access the brain, such compounds are useful in attenuating behavioral responses indicative of persistent pain in rodent models of inflammation. The present invention also sets forth methods for inhibiting FAAH as well as methods for treating conditions such as, but not limited to, pain, inflammation, immune disorders, dermatitis, mucositis, the over reactivity of peripheral sensory neurons, neurodermatitis, and an overactive bladder. Accordingly, the invention also provides compounds, methods, and pharmaceutical compositions for treating conditions in which the selective inhibition of peripheral FAAH (as opposed to CNS FAAH) would be of benefit.

2. Definitions

It is noted here that as used in this specification and the appended claims, the singular forms "a," "an," and "the" include plural reference unless the context clearly dictates otherwise.

Figure 1:
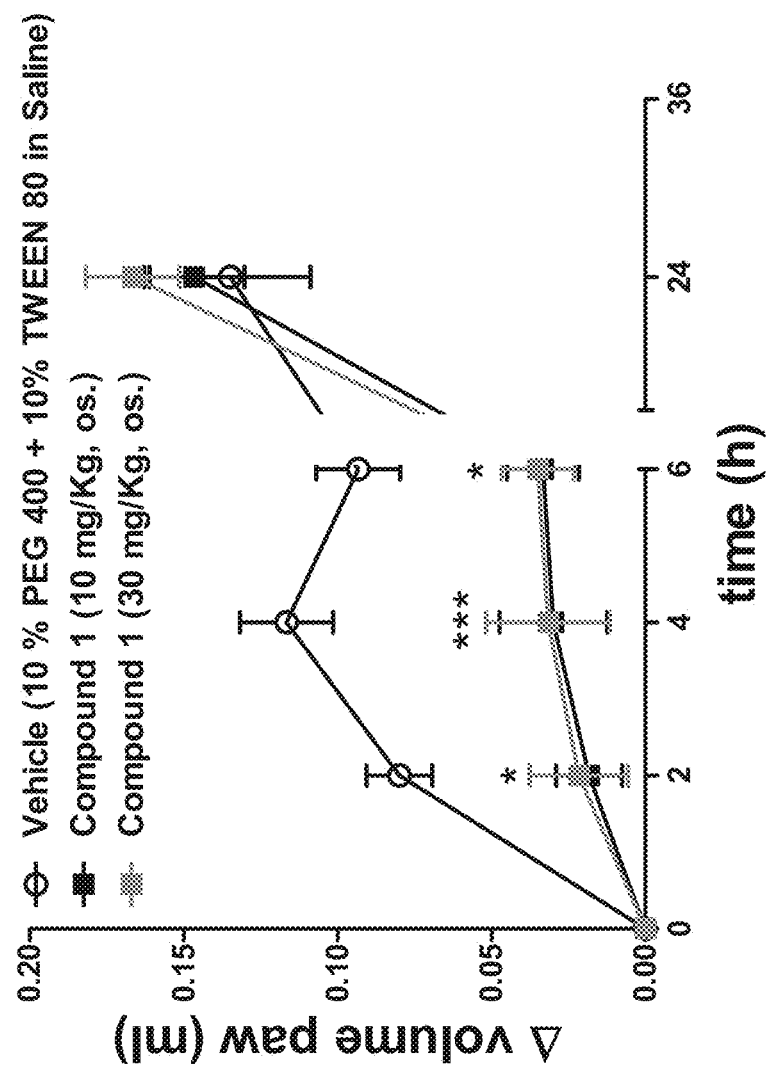
FIG. 1 Effects of oral administration of compound 1 on carrageenan-induced edema. Compound 1 reduced the difference between the paw volume of male CD1 mice, measured at each time point, and the basal paw volume measured immediately before carrageenan injection. Results are expressed as mean±SEM (n=6, each group), * $p<0.05$, $p<0.001$ vs. vehicle.
Figure 2:
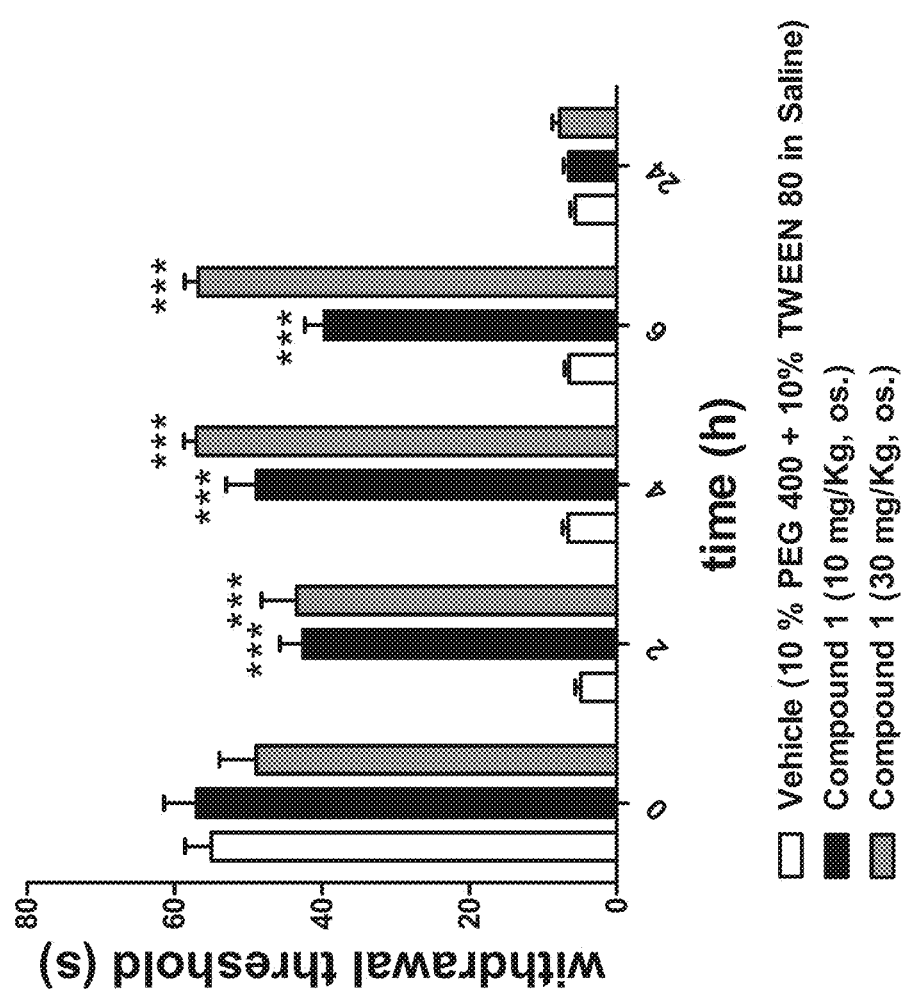
FIG. 2 Effects of oral administration of compound 1 on carrageenan-induced hyperalgesia. In the mechanical hyperalgesia test, compound 1 increased the withdrawal threshold measured on the inflamed ipsilateral paw at different time points after oral drug administration. Results are expressed as mean±SEM (n=6, each group), *** $p<0.001$ vs. vehicle.
Figure 3:
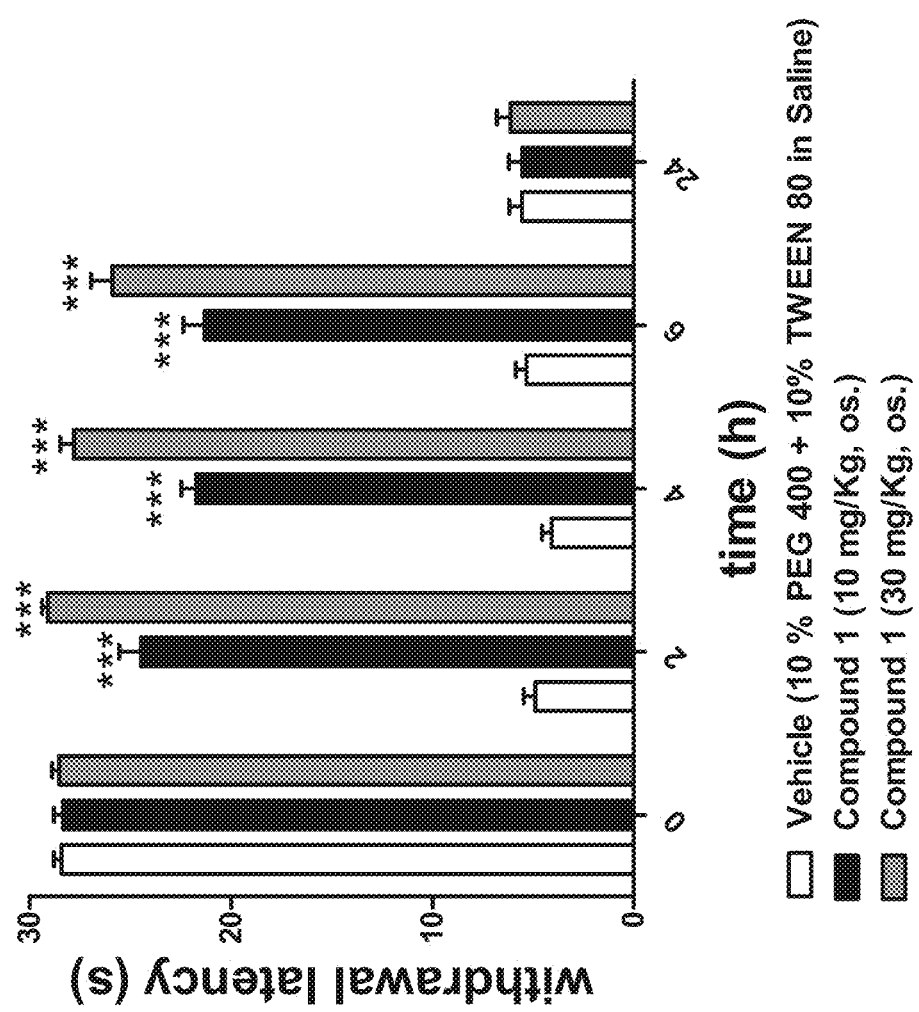
FIG. 3 Effects of oral administration of compound 1 on carrageenan-induced hyperalgesia. In the thermal hyperalgesia test, compound 1 increased the withdrawal threshold measured on the inflamed ipsilateral paw at different time points after oral drug administration. Results are expressed as mean±SEM (n=6, each group), *** $p<0.001$ vs. vehicle.

"FAAH" denotes a mammalian Fatty Acid Amide Hydrolase and includes, but is not limited to, the human, rat, and mouse forms of the enzyme. U.S. Pat. No. 6,271,015 discloses isolated and purified forms of FAAH. In one set of embodiments, the FAAH IC$_{50}$ of the subject compounds is defined according to inhibition of the rat enzyme under physiologically relevant conditions. Fatty Amide Hydrolases (FAAHs) (Deutsch, D. G., et al., *Prostaglandins Leukot. Essent. Fatty Acid,* 66, 201-210 (2002)) are enzymes responsible for the degradation of lipid ethanolamides, (Fowler, C. J., et al., *Biochem. Pharmacol.* 62, 517-526 (2001); Patricelli, M. P., et al. *Vitam. Horm.,* 62, 663-674 (2001)) e.g. anandamide (AEA, 1, FIG. 1), (Devane, W. A., et al., *Science* 258, 1946-1949 (1992)) oleoylethanolamide, (Rodríguez de Fonseca, F., et al. *Nature (London)* 414, 209-212 (2001); Fu, J., et al., *Nature (London)* 425, 90-93 (2003)) and palmitoylethanolamide, (Calignano, A., et al. *Nature (London)* 394, 277-281 (1998); Lambert, D. M., et al., *Curr. Med. Chem.* 9, 663-674 (2002) a biochemical process which, along with selective transport into cells in the case of AEA, (Di Marzo, V., *Nature (London)* 372, 686-691 (1994); Beltrama, M., et al., *Science* 277, 1094-1097 (1997); Piomelli, D., et al., *Proc. Natl. Acad. Sci. U.S.A.* (2002)) brings about the cessation of the cellular effects of these autacoids. Owing to the various and important physiological roles of fatty acid ethanolamides, classes of small-molecule compounds able to block FAAH or FAAHs but not bind to other endocannabinoid-metabolizing enzymes, e.g. monoglyceride lipase (MGL), (Dinh, T. P., et al., *Proc. Natl. Acad. Sci. U.S.A.* 99, 10819-10824 (2002)) or cannabinoid receptors, would be advantageous both as pharmacological tools and as prototypes for drug development projects (Piomelli, D., et al. *Trends Pharmacol. Sci.* 21, 218-224 (2000); Bisogno, T., et al., *Curr. Pharm. Des.* 8, 533-547 (2002); Yarnell, A., *Chem. Eng. News* 80(49), 32 (2002); Smith, A., *Nat. Rev. Drug Discov.* 2, 92 (2003); Wendeler, M., et al. *Angew. Chem. Int. Ed.* 42, 2938-2941 (2003)).

The term "pharmaceutically acceptable carrier" encompasses any of the standard pharmaceutical carriers, buffers and excipients, including phosphate-buffered saline solution, water, and emulsions (such as an oil/water or water/oil emulsion), and various types of wetting agents and/or adjuvants. Suitable pharmaceutical carriers and their formulations are described in Remington's Pharmaceutical Sciences (Mack Publishing Co., Easton, 19th ed. 1995). Preferred pharmaceutical carriers depend upon the intended mode of administration of the active agent. Typical modes of administration are described below.

The term "effective amount" means a dosage sufficient to produce a desired result with respect to the indicated disorder, condition, or mental state. The desired result may comprise a subjective or objective improvement in the recipient of the dosage. With respect to pain, the improvement may be decreased sign or symptom of pain.

The terms "treatment", "therapy" and the like include, but are not limited to, methods and manipulations to produce beneficial changes in a recipient's health status. The changes can be either subjective or objective and can relate to features such as symptoms or signs of the disease, disorder or condition being treated. For example, if the patient notes decreased pain, then successful treatment of pain has occurred. For example, if a decrease in the amount of swelling has occurred, then a beneficial treatment of inflammation has occurred. Similarly, if the clinician notes objective changes, such as improved range of motion, then treatment for a pain or inflammation which had been impairing the motion has also been beneficial. Preventing the deterioration of a recipient's status is also included by the term.

Therapeutic benefit includes any of a number of subjective or objective factors indicating a beneficial response or improvement of the condition being treated as discussed herein.

"Pharmaceutically-acceptable" or "therapeutically-acceptable" refers to a substance which does not interfere with the effectiveness or the biological activity of the active ingredients and which is not toxic to the hosts in the amounts used, and which hosts may be either humans or animals to which it is to be administered.

"Therapeutically-effective amount" refers to the amount of an active agent sufficient to induce a desired biological or clinical result. That result may be alleviation of the signs, symptoms, or causes of a disease, or any other desired alteration of a biological system. The term "therapeutically effective amount" is used herein to denote any amount of the formulation which causes a substantial improvement in a disease, disorder or condition when administered to a subject. The amount will vary with the condition being treated, the stage of advancement of the condition, and the type and concentration of formulation applied. Appropriate amounts in any given instance will be readily apparent to those skilled in the art or capable of determination by routine experimentation.

A "prophylactic treatment" is a treatment administered to a subject who does not exhibit signs of a neurological or psychological disorder or condition or exhibits only early or slight signs of such a disorder or condition, wherein treatment is administered for the purpose of decreasing the risk of developing a pathology or worsening of disorder or condition. The compounds of the invention may be given as a prophylactic treatment to prevent undesirable or unwanted anxiety or panic attacks, or to reduce the level of anxiety should worsening occur.

The term "subject" as used herein includes any animal, including, but not limited to, mammals (e.g., rat, mouse, cat, dog) including humans to which a treatment is to be given.

As used herein, the term "hydrocarbyl" refers to a ($C_1$-$C_8$) hydrocarbon radical that is a ($C_1$-$C_8$)alkyl, ($C_1$-$C_8$)alkenyl, ($C_3$-$C_8$)cycloalkyl, ($C_3$-$C_8$)cycloalkenyl, ($C_1$-$C_8$)heteroalkyl, ($C_1$-$C_8$)heteroalkenyl, ($C_3$-$C_8$)heterocycloalkyl, or ($C_3$-$C_8$)heterocycloalkenyl radical. More preferably, the hydrocarbyl in each instance is either a substituted or unsubstituted ($C_1$ to $C_6$), ($C_1$ to $C_3$), or ($C_1$ to $C_2$)hydrocarbyl, and more preferably still an unsubstituted ($C_1$ to $C_3$)alkyl. Still more preferably the hydrocarbyl in each instance is methyl or ethyl or trifluoromethyl. The term "hydrocarbyl" also includes those groups having up to 1, 2, or 3 atoms of a hydrocarbyl group as set forth above replaced by a heteroatom with the proviso that the heteroatoms of the hydrocarbyl are not contiguous to each other and the hydrocarbyl is not attached to the remainder of the compound by a heteroatom of the hydrocarbyl.

As used herein, the term "alkyl", by itself or as part of another substituent, means, unless otherwise stated, a straight or branched chain, saturated, hydrocarbon radical, having the number of carbon atoms designated (i.e. ($C_1$-$C_6$) means one to six carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like.

As used herein, the term "alkoxy" represents an alkyl moiety joined to the remainder of the molecule by the oxygen atom of the alkoxy. Accordingly, examples of alkoxy would include, but not be limited to, methoxy, ethoxy, propoxy and the like.

As used herein, the term "carboxy" or "carboxyl" refers to a compound having the general formula R—COOH wherein R is an organic molecule such as alkyl. Examples of carboxy include —COOH; —CH$_2$—COOH, and —CH$_2$—CH$_2$—COOH.

The term "alkenyl" is derived from the name of the corresponding alkyl group but differs in possessing one or more double bonds. Similarly, "alkynyl" groups are named with respect to their corresponding alkyl group but differ in possessing one or more triple bonds. Non-limiting examples of such unsaturated alkenyl groups and alkynyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

As used herein, the term "heteroalkyl" derives its name from the corresponding alkyl group but differs in containing one, two, or three heteroatoms independently selected from N, O, and S each substituting for a carbon of an alkyl group. The heteroatom nitrogen and sulfur atoms are optionally oxidized, and the nitrogen atom(s) are optionally quaternized. A heteroalkyl group is attached to the remainder of the molecule through a carbon atom of the heteroalkyl group and the heteroatoms of the heteroalkyl are not contiguous with another heteroatom.

The term "heteroalkenyl" derives its name from the corresponding alkenyl group but differs in having 1, 2, or 3 heteroatoms substituting for a carbon of the alkenyl group. The heteroatom nitrogen and sulfur atoms are optionally oxidized, and the nitrogen atom(s) are optionally quaternized. A heteroatom can form a double bond with a carbon atom. A heteroalkenyl group is attached to the remainder of the molecule through a carbon atom of the hydrocarbyl and the heteroatoms of the hydrocarbyl are not contiguous with another heteroatom.

As used herein, the term "cycloalkyl" refers to a saturated monocyclic hydrocarbon radical comprising from about 3 to about 8 carbon atoms, and more preferably 3 to 6 carbon atoms. The term "cycloalkenyl" refers to monocyclic, non-aromatic hydrocarbon radical comprising from about 5 to about 6 carbon atoms and having at least one double bond. Exemplary cycloalkyl groups and cycloalkenyl groups include cyclopropyl, cyclobutyl, cyclopentyl, cyclohexyl, cyclohexenyl, cyclohepta-1,3-dienyl, and the like.

As used herein, the term "heterocycloalkyl" refers to a saturated or partially unsaturated monocyclic hydrocarbon radical comprising from about 3 to about 8 carbon atoms, and more preferably 3 to 6 carbon atoms in which 1, 2 or 3 of the carbon atoms are independently replaced by a heteroatom independently selected from O, N, or S. Nitrogen and sulfur atoms are optionally oxidized, and the nitrogen atom(s) are optionally quaternized. Sulfur maybe in the thio, sulfinyl or sulfonyl oxidation state. The term "heterocycloalkenyl" refers to heterocycloalkyl group having at least one double bond. A heterocycloalkyl or heterocycloalkenyl group is attached to the remainder of the molecule through a carbon atom, respectively, of the heterocycloalkyl or heterocycloalkenyl group; and the heteroatoms of the heterocycloalkyl or heterocycloalkenyl are not contiguous with another heteroatom of the heterocycloalkyl or heterocycloalkenyl.

As used herein, the term "heteroatom" is meant to include oxygen (O), nitrogen (N), and sulfur (S)).

As used herein, the term "halogen" or "halo" refers to iodine (I), bromine (Br), chlorine (Cl), and/or fluorine (F).

The above hydrocarbyl, alkyl, alkenyl, cycloalkyl, cycloalkenyl, heteroalkyl, heteroalkenyl, cycloheteroalkyl, and cycloheteroalkenyl radicals can each be substituted with one, two or three substituents independently selected from unsubstituted (C$_1$-C$_6$) or (C$_1$-C$_3$)alkyl, unsubstituted (C$_1$-C$_6$) or (C$_1$-C$_3$)alkoxy, unsubstituted amino, unsubstituted (C$_1$-C$_6$) or (C$_1$-C$_3$) alkylamino, di-unsubstituted (C$_1$-C$_6$) or (C$_1$-C$_3$)alkylamino, hydroxy, halo, unsubstituted carboxamido, unsubstituted (C$_1$-C$_6$) or (C$_1$-C$_3$)alkylcarboxamido, oxo, and nitro. Non-limiting examples of alkoxy groups include methoxy, ethoxy, t-butoxy, cyclopentyloxy, trifluoromethoxy, and the like. As used herein, the term "oxo" refers to =O. As used herein, the term "amino" refers to —NH$_2$. In some embodiments, each of the hydrocarbyl groups is unsubstituted. In some embodiments, each of the hydrocarbyl, alkyl, alkenyl, cycloalkyl, cycloalkenyl, heteroalkyl, heteroalkenyl, cycloheteroalkyl, and cycloheteroalkenyl groups are unsubstituted.

A peripherally restricted compound is one which poorly penetrates the blood brain barrier or is extruded more rapidly from the brain. Accordingly, a peripherally restricted compound according to the invention can be administered at dosages which inhibit FAAH activity in the periphery to a far greater extent than centrally (e.g., in brain). In some embodiments, the FAAH inhibitor according to the invention has a subcutaneously, intravenously, or orally administered ED$_{50}$ for inhibiting peripheral FAAH activity (e.g., liver) which is no more than ¼, ⅛, or 1/10 of the ED$_{50}$ for inhibiting brain FAAH activity in the mouse. Preferably, the peripherally restricted FAAH inhibitor is one which reduces FAAH activity in the periphery by at least 3, 4, 5, 7-, 8-fold, or 10-fold more than it reduced FAAH activity centrally (e.g., in the brain) of the test mammal. For instance, FAAH activity levels in the periphery can be inhibited by 80% (20% of the baseline or uninhibited level of FAAH activity remains) while central FAAH activity would be inhibited by 10% (90% of the baseline or uninhibited level of FAAH activity remains) providing for a 80%/10% or 8-fold difference in FAAH inhibition.

A "physiologically cleavable ester" or "physiologically hydrolysable ester" is one which is a substrate for carboxyesterases in vivo. Physiologically cleavable esters are typically rapidly hydrolyzed such that the concentration of the corresponding alcohol or acid released by the hydrolysis comes to approach or exceed that of the ester in blood or plasma. For instance, a physiologically cleavable ester is one which is rapidly hydrolyzed to the corresponding alcohol and acid in vivo with a half time of less than ½, 1, 2, 3 or 4 hours at a therapeutically relevant dosages. See e.g., Bundgaard, H., Ed., Design of Prodrugs (Elsevier Science Publishers, Amsterdam 1985). A physiologically cleavable ester refers to those esters which retain, upon hydrolysis of the ester bond, the biological effectiveness and properties of the carboxylic acid or alcohol and are not biologically or otherwise undesirable. For a description of pharmaceutically acceptable esters as prodrugs, see Bundgaard, H., supra. These esters are typically formed from the reaction of a corresponding carboxylic acid (X—CO$_2$H) or an alcohol (X—OH), respectively, with a compound according to the invention which respectively is an alcohol or acid. X can be a substituted or unsubstituted hydrocarbyl, a (C$_1$-C$_3$)alkyl, a (C$_1$ to C$_6$)alkyl (e.g., ethyl), aryl, heteroaryl, cycloalkyl, alkenyl, cycloalkenyl, heteroalkyl, heteroalkenyl, cycloheteroalkyl, and cycloheteroalkenyl radical. Pharmaceutically acceptable alcohols and acids are contemplated (e.g., ethanol, benzoic acid).

3. Compounds

The present application provides peripherally restricted FAAH inhibitors of Formula I. These inhibitors retain a FAAH inhibitory activity and are peripherally restricted which is highly advantageous because these inhibitors do not substantially form reactive benzoquinones when metabolized in a mammalian subject.

In some embodiments, the peripheral preference of the FAAH inhibitors is specifically conferred by certain meta-substituents on the proximal phenyl of the biphenyl moiety. In some embodiments, meta-substituents include the hydroxyl, hydroxymethyl, and carboxyl group as well as the hydrolysable esters thereof. In certain embodiments, the meta-substituents are hydroxyl. In other embodiments, the met-substituents are hydroxymethyl. In yet other embodiments, the meta-substituents are carboxyl.

In certain embodiments, the present invention provides compounds are according to the formula:

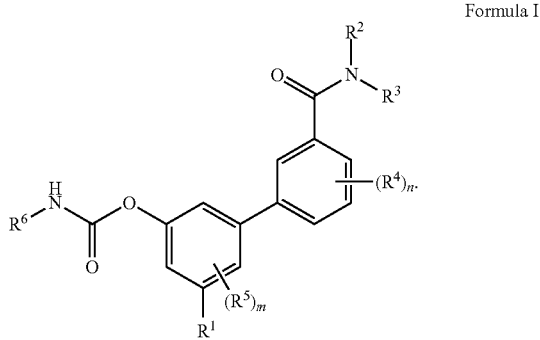

Formula I

In Formula I, $R^1$ is selected from the group consisting of hydrogen, hydroxy and the physiologically hydrolyzable esters thereof, —SH, carboxy and the physiologically hydrolysable esters thereof, hydroxy($C_1$-$C_3$)alkyl (e.g., —$CH_2OH$ and —$CH_2CH_2OH$) and the physiologically hydrolyzable esters thereof, —$NR^7R^8$, and —$NHSO_2R^9$; wherein $R^7$ and $R^8$ are independently selected from hydrogen or ($C_1$-$C_3$) alkyl and $R^9$ is selected from hydrogen, methyl, ethyl, trifluoromethyl or trifluoroethyl; $R^2$ and $R^3$ are independently selected from hydrogen or substituted or unsubstituted ($C_1$-$C_3$)alkyl; each $R^4$ is independently a hydrogen, a substituted or unsubstituted ($C_1$-$C_3$)alkyl and n is an integer from 0 to 4; each $R^5$ is independently hydrogen, halogen, hydroxy and the physiologically hydrolyzable esters thereof, carboxy and the physiologically hydrolysable esters thereof, hydroxyl-($C_1$-$C_3$)alkyl and the physiologically hydrolyzable esters thereof, —($C_1$-$C_3$)alkoxy, or —$NR^{20}R^{21}$; and $R^{20}$ and $R^{21}$ are independently selected from hydrogen or ($C_1$-$C_3$) alkyl; m is an integer from 0 to 3; $R^6$ is an unsubstituted or substituted cyclohexyl, cyclopentyl, cyclobutyl or tetrahydropyran-4-yl. Also included are the pharmaceutically acceptable salts thereof.

In some embodiments of the above compounds, m and n are each 0, and $R^2$ and $R^3$ are each H.

In further embodiments of any of the above compounds, $R^1$ is hydroxy, carboxy, or hydroxymethyl.

In some embodiments, $R^1$ hydrogen. In certain embodiments, $R^1$ is hydroxy or the physiologically hydrolyzable esters thereof. In other embodiments, $R^1$ is —SH. In still other embodiments, $R^1$ is carboxy or the physiologically hydrolyzable esters thereof. In certain embodiments, $R^1$ is hydroxyl-($C_1$-$C_3$)alkyl. In other embodiments, $R^1$ is —$CH_2OH$ or —$CH_2CH_2OH$ or the physiologically hydrolyzable esters thereof. In certain embodiments, $R^1$ is —$NR^7R^8$. In other embodiments, $R^1$ is —$NHSO_2R^9$. In some of these embodiments, $R^7$ and $R^8$ are independently hydrogen or ($C_1$-$C_3$)alkyl. In some embodiments, $R^7$ and $R^8$ are independently methyl, ethyl, propyl, isopropyl, butyl, t-butyl, isobutyl, n-butyl, pentyl, hexyl, heptyl, or octyl. In certain embodiments, $R^9$ is hydrogen, methyl, ethyl, trifluoromethyl or trifluoroethyl.

In still further embodiments of any of the above compounds, $R^6$ is substituted or unsubstituted. In still further embodiments of any of the above compounds, $R^6$ is cyclohexyl.

In yet further embodiments of any of the above compounds, the cyclohexyl is unsubstituted.

In still further embodiments, the compound is a physiologically acceptable ester of any of the above.

In still further embodiments of any of the above, $R^7$ and $R^8$ are each H and $R^9$ is methyl, ethyl, trifluoromethyl or trifluoroethyl.

In other embodiments of the compounds of Formula I, m is 0 and n is 0, 1, 2, 3, or 4. In other further embodiments, m is 1 and n is 0, 1, 2, 3, or 4. In still other embodiments, m is 2 and n is 0, 1, 2, 3, or 4. In yet still other embodiments, m is 3, and n is 0, 1, 2, 3, or 4. In some further embodiments, the sum of m and n is 0, 1, 2, or 3. In still further embodiments, of each of the above, each $R^1$, $R^2$, $R^3$, $R^4$, $R^6$, $R^7$, and $R^8$ member is also unsubstituted.

In some embodiments, $R_1$ is hydroxy or a hydroxy($C_1$-$C_3$)alkyl group or a physiologically hydrolysable ester of the hydroxyl or hydroxy($C_1$-$C_3$)alkyl group. In certain embodiments, $R^1$ has the formula —$OC(O)R^{10}$, —$(O)COR^{10}$, —$CH_2OC(O)R^{10}$, —$CH_2(O)COR^{10}$, —$CH_2CH_2OC(O)R^{10}$, $CH_2CH_2(O)COR^{10}$, —$CH(CH_3)(O)COR^{10}$), —$CH(CH_3)(O)COR^{10}$. In these formula, $R^{10}$ is substituted or unsubstituted hydrocarbyl. In other embodiments, $R^{10}$ is substituted or unsubstituted alkyl, alkenyl, cycloalkyl, heteroalkyl, heterocycloalkyl, heteroalkenyl, heterocycloalkenyl, and cycloalkenyl. In other embodiments, $R^{10}$ is substituted or unsubstituted ($C_1$-$C_3$)alkyl. In still other embodiments, $R^{10}$ is methyl, ethyl, propyl, or trifluoromethyl. In yet other embodiments, $R^{10}$ is a substituted or unsubstituted ($C_1$-$C_3$) hydrocarbyl selected from the group consisting of alkenyl, cycloalkyl, heteroalkyl, heterocycloalkyl, heteroalkenyl, heterocycloalkenyl, and cycloalkenyl. In further of these embodiments, m is 0 and n is 0, 1, 2; m is 1 and n is 0, 1, or 2; or m is 2 and n is 0, 1, or 2.

Preferably, in the case where $R^1$ is a carboxy group or physiologically hydrolysable ester thereof, $R^1$ is —$CO_2H$, or —$CO_2R^{10}$ wherein $R^{10}$ is substituted or unsubstituted hydrocarbyl, more preferably, substituted or unsubstituted alkyl, alkenyl, cycloalkyl, heteroalkyl, heterocycloalkyl, heteroalkenyl, heterocycloalkenyl, and cycloalkenyl and still more preferably, substituted or unsubstituted ($C_1$-$C_3$) alkyl (e.g., methyl, ethyl, propyl, trifluoromethyl) or a substituted or unsubstituted ($C_1$-$C_3$) hydrocarbyl selected from alkenyl, cycloalkyl, heteroalkyl, heterocycloalkyl, heteroalkenyl, heterocycloalkenyl, and cycloalkenyl. In further of these embodiments, m is 0 and n is 0, 1, 2; m is 1 and n is 0, 1, or 2; or m is 2 and n is 0, 1, or 2.

In further embodiments that are applicable to any of the above, $R^2$ and $R^3$ are hydrogen. In further of these embodiments, m is 0 and n is 0, 1, or 2; m is 1 and n is 0, 1, or 2; or m is 2 and n is 0, 1, or 2. In further of these embodiments, m is 0 and n is 0, 1, 2; m is 1 and n is 0, 1, or 2; or m is 2 and n is 0, 1, or 2.

In further embodiments that are applicable to any of the above, $R^1$ is hydroxy and at least one of $R^2$ and $R^3$ is hydrogen. In still further embodiments of such, both of $R^2$ and $R^3$ are hydrogen. In other embodiments in which $R^1$ is hydroxy, $R^2$ and $R^3$ are independently selected from substituted or unsubstituted ($C_1$-$C_3$)alkyl (e.g., methyl, ethyl, propyl), and H. In further of these embodiments, m is 0 and n is 0, 1, 2; m is 1 and n is 0, 1, 2; or m is 2 and n is 0, 1, 2.

In yet still further embodiments that are applicable to any of the above, $R^6$ is substituted or unsubstituted cyclohexyl. Substituents for the cyclohexyl include alkyl (e.g., methyl, ethyl), halo (F, Cl, I, Br and preferably F or Cl), and trifluoromethyl. In yet other of these embodiments, m is 0 and n is 0, 1, 2; m is 1 and n is 0, 1, 2; or m is 2 and n is 0, 1, 2.

In a particularly preferred embodiment, $R^1$ is hydroxy or hydroxy($C_1$-$C_3$)alkyl or a physiologically hydrolyzable ester thereof in which the hydrolysis releases the corresponding compound wherein $R^1$ is hydroxyl or hydroxy($C_1$-$C_3$)alkyl, $R^6$ is unsubstituted cyclohexyl, m is 0 and n is 0, 1, or 2; or m is 1 and n is 0, 1, or 2, or m is 2 and n is 0, 1, or 2. In still further embodiments, $R^2$ and $R^3$ are each H. In some embodiments of such the ester is of the formula —OC(O)$R^{10}$ wherein $R^{10}$ is substituted or unsubstituted hydrocarbyl, more preferably, substituted or unsubstituted alkyl, alkenyl, cycloalkyl, heteroalkyl, heterocycloalkyl, heteroalkenyl, heterocycloalkenyl, and cycloalkenyl and still more preferably, substituted or unsubstituted ($C_1$-$C_3$)alkyl (e.g., methyl, ethyl, propyl, trifluoromethyl) or a substituted or unsubstituted ($C_1$-$C_3$) hydrocarbyl selected from alkenyl, cycloalkyl, heteroalkyl, heterocycloalkyl, heteroalkenyl, heterocycloalkenyl, and cycloalkenyl. In some further embodiments, $R^{10}$ is unsubstituted hydrocarbyl, unsubstituted alkyl, unsubstituted alkenyl, unsubstituted cycloalkyl, unsubstituted heteroalkyl, unsubstituted heterocycloalkyl, unsubstituted heteroalkenyl, unsubstituted heterocycloalkenyl, or unsubstituted cycloalkenyl; or unsubstituted ($C_1$-$C_3$)alkyl (e.g., methyl, ethyl, propyl, trifluoromethyl) or unsubstituted ($C_1$-$C_3$) hydrocarbyl selected from alkenyl, cycloalkyl, heteroalkyl, heterocycloalkyl, heteroalkenyl, heterocycloalkenyl, and cycloalkenyl.

In some embodiments of formula (I), $R^5$ is independently hydrogen, halogen, hydroxy and the physiologically hydrolyzable esters thereof, carboxy and the physiologically hydrolyzable esters thereof, hydroxyl-($C_1$-$C_3$)alkyl and the physiologically hydrolyzable esters thereof, —($C_1$-$C_3$) alkoxy, or —$NR^{20}R^{21}$; and $R^{20}$ and $R^{21}$ are independently selected from hydrogen or ($C_1$-$C_3$)alkyl. In some other embodiments, $R^5$ is independently selected from hydrogen or halogen. In certain embodiments, $R^5$ is independently hydrogen, halogen, or hydroxy and the physiologically hydrolyzable esters thereof. In other embodiments, $R^5$ is independently hydroxy and the physiologically hydrolyzable esters thereof, carboxy and the physiologically hydrolysable esters thereof, hydroxyl-($C_1$-$C_3$)alkyl and the physiologically hydrolyzable esters thereof, or —($C_1$-$C_3$)alkoxy. In yet other embodiments, $R^5$ is hydroxy and the physiologically hydrolyzable esters thereof. In still other embodiments, $R^5$ is carboxy and the physiologically hydrolysable esters thereof. In other embodiment, $R^5$ is hydroxyl-($C_1$-$C_3$)alkyl and the physiologically hydrolyzable esters thereof. In some embodiments, $R^5$ is —($C_1$-$C_3$)alkoxy. In some other embodiments, $R^5$ is $NR^{20}R^{21}$ and $R^{20}$ and $R^{21}$ are independently selected from hydrogen or ($C_1$-$C_3$)alkyl. In some embodiments, $R^5$ is —$NR^{20}R^{21}$ and $R^{20}$ and $R^{21}$ are hydrogen. In still other embodiments, $R^5$ is as described herein and m is 1.

In some embodiments of formula (I), $R^5$ is independently —($C_1$-$C_3$)alkoxy or —$NR^{20}R^{21}$; and $R^{20}$ and $R^{21}$ are independently selected from hydrogen or ($C_1$-$C_3$)alkyl. In other embodiments of formula (I), $R^5$ is independently hydrogen, halogen, hydroxy and the physiologically hydrolyzable esters thereof, or carboxy and the physiologically hydrolysable esters thereof. In some embodiments of formula (I), $R^5$ is independently hydrogen, hydroxy and the physiologically hydrolyzable esters thereof, carboxy and the physiologically hydrolysable esters thereof, or hydroxyl-($C_1$-$C_3$)alkyl and the physiologically hydrolyzable esters thereof.

In some embodiments, $R^5$ is hydroxyl. In certain embodiments, $R^5$ is hydroxyl and m is 1. In some embodiments, $R^5$ is COOH. In certain other embodiments, $R^5$ is COOH and m is 1. In some other embodiments, $R^5$ is $CH_2OH$. In some embodiments, $R^5$ is $CH_2OH$ and m is 1. In some other embodiments, $R^5$ is $OCH_3$. In other embodiments, $R^5$ is $OCH_3$ and m is 1. In certain embodiments, $R^5$ is $CH_3$. In certain other embodiments, $R^5$ is $CH_3$ and m is 1. In some embodiments, $R^5$ is F. In certain embodiments, $R^5$ is F and m is 1. In other embodiments, $R^5$ is $NH_2$. In some other embodiments, $R^5$ is $NH_2$ and m is 1.

In a particularly preferred embodiment, the compound has a formula selected from the group consisting of:

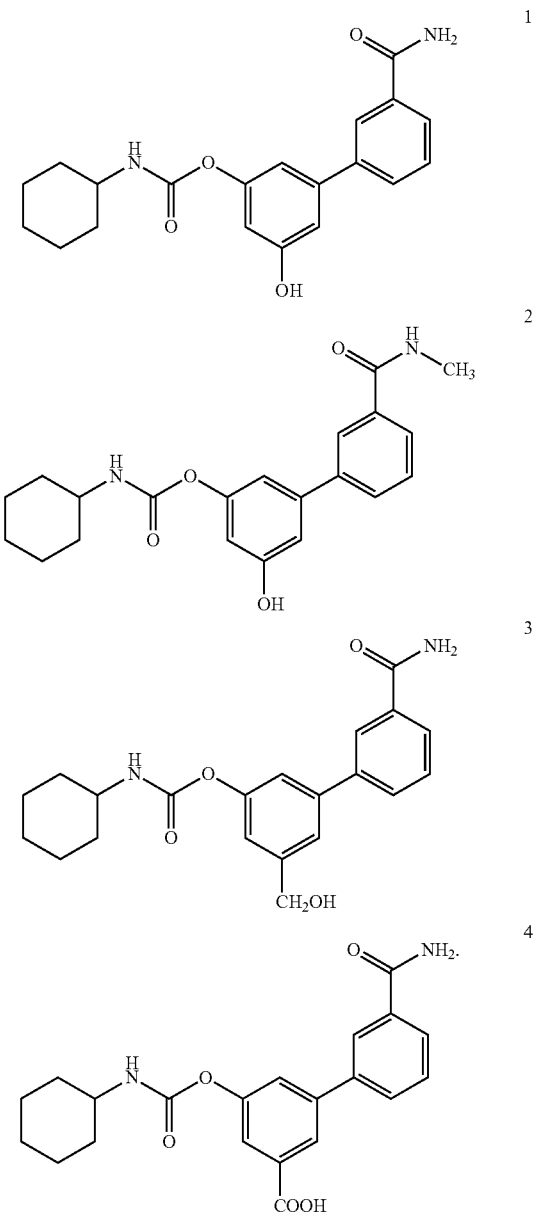 [SMILES: NC(=O)c1cccc(-c2cc(O)cc(OC(=O)NC3CCCCC3)c2)c1 ; CNC(=O)c1cccc(-c2cc(O)cc(OC(=O)NC3CCCCC3)c2)c1 ; NC(=O)c1cccc(-c2cc(CO)cc(OC(=O)NC3CCCCC3)c2)c1 ; NC(=O)c1cccc(-c2cc(OC(=O)NC3CCCCC3)cc(C(=O)O)c2)c1]

In further embodiments, the above compound is provided as a physiologically hydrolysable ester as described above.

In preferred embodiments of any of the above compounds are peripherally restricted compounds.

In some embodiments, the present invention provides a compound having the following structure:

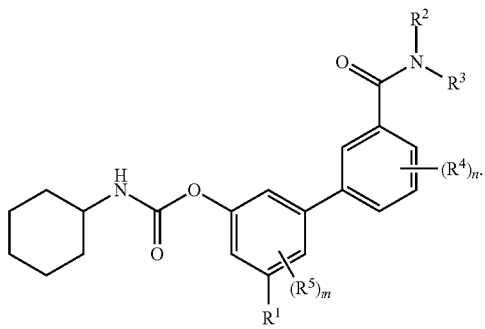

In other embodiments, the present invention provides a compound having the following structure:

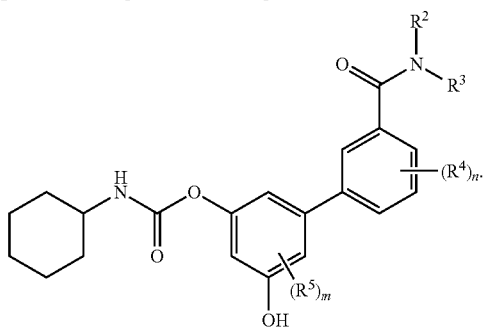

In some other embodiments, the present invention provides a compound having the following structure:

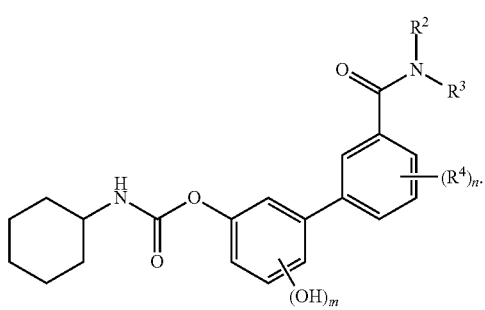

In certain embodiments, the present invention provides a compound having the following structure:

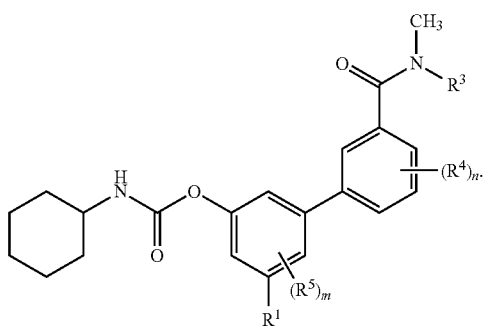

In some embodiments, the present invention provides a compound having the following structure:

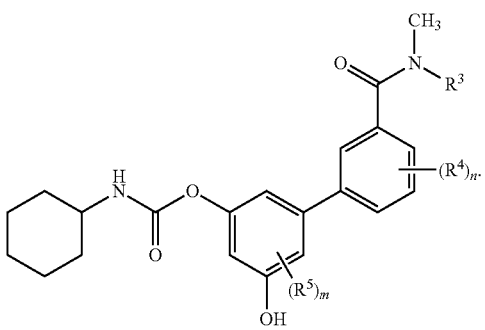

In other embodiments, the present invention provides a compound having the following structure:

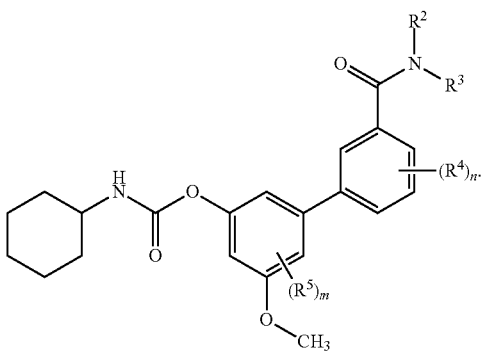

In some other embodiments, the present invention provides a compound having the following structure:

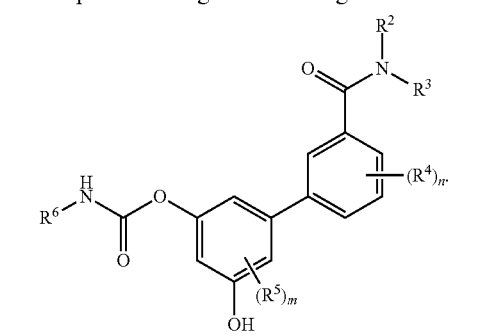

In yet other embodiments, the present invention provides a compound having the following structure:

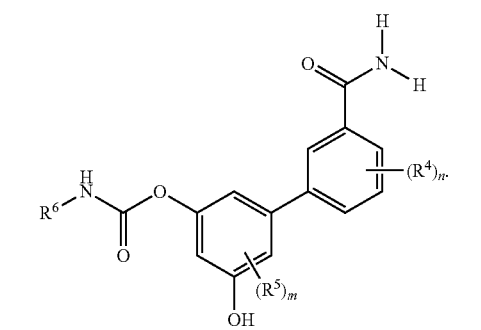

In certain embodiments, the present invention provides a compound having the following structure:

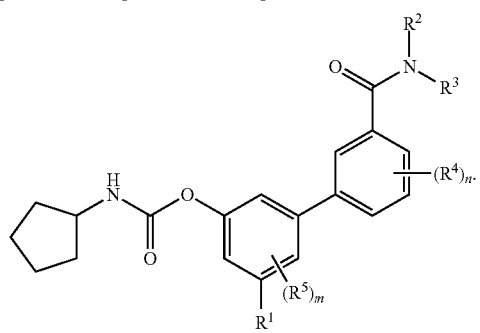

In other embodiments, the present invention provides a compound having the following structure:

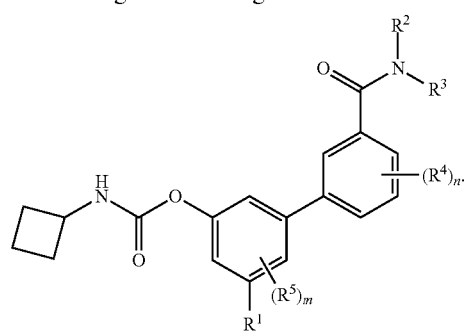

In some embodiments, the present invention provides a compound having the following structure:

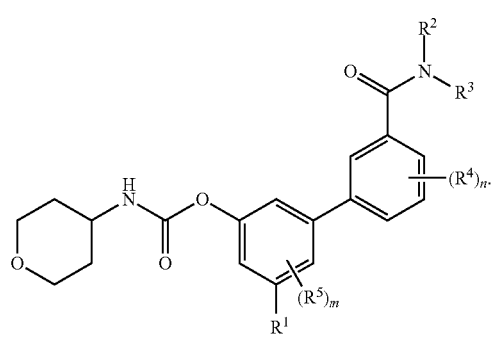

In some other embodiments, the present invention provides a compound having the following structure:

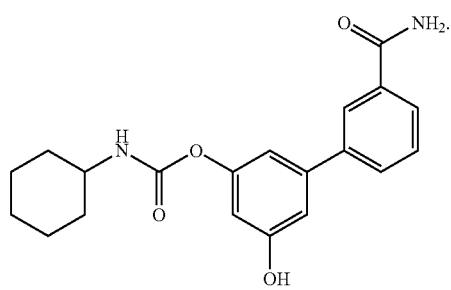 [SMILES: NC(=O)c1cccc(-c2cc(O)cc(OC(=O)NC3CCCCC3)c2)c1]

In yet other embodiments, the present invention provides a compound having the following structure:

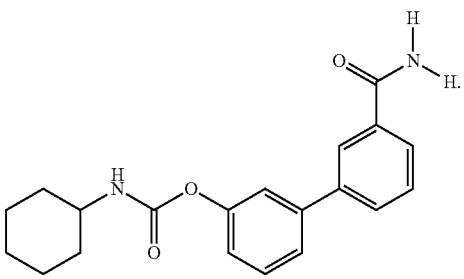

In some embodiments, the present invention provides a compound having the following structure:

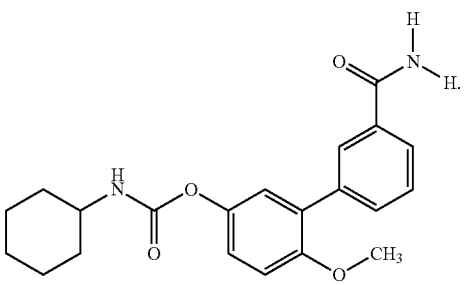

In other embodiments, the present invention provides a compound having the following structure:

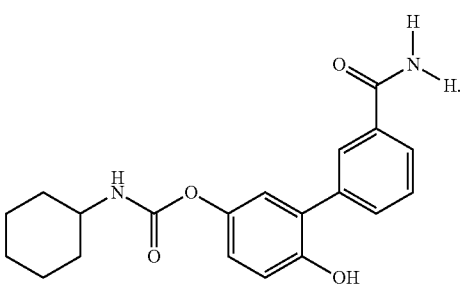

In certain embodiments, the present invention provides a compound having the following structure:

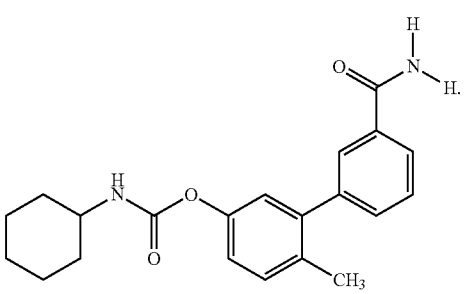

In some embodiments, the present invention provides a compound having the following structure:

In certain other embodiments, the present invention provides a compound having the following structure:

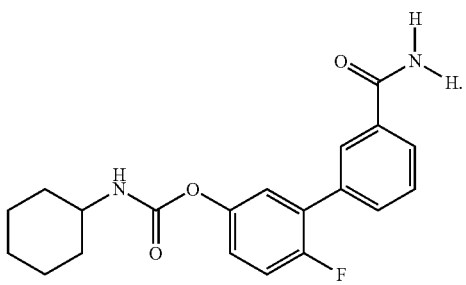

In some embodiments, the present invention provides a compound having the following structure:

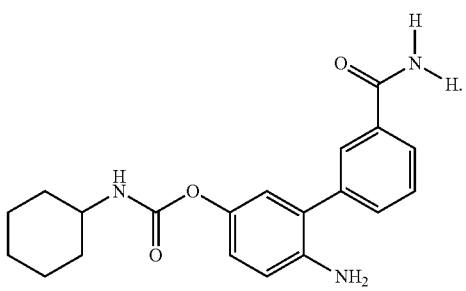

In some other embodiments, the present invention provides a compound having the following structure:

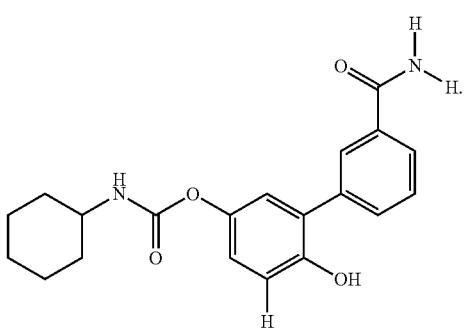

In yet other embodiments, the present invention provides a compound having the following structure:

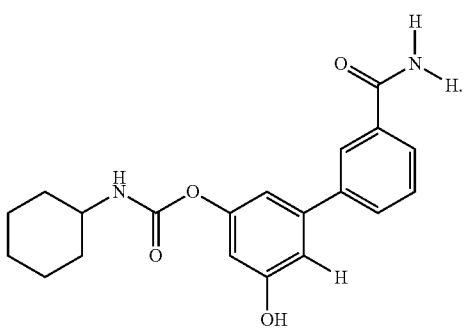

In some embodiments, the present invention provides a compound having the following structure:

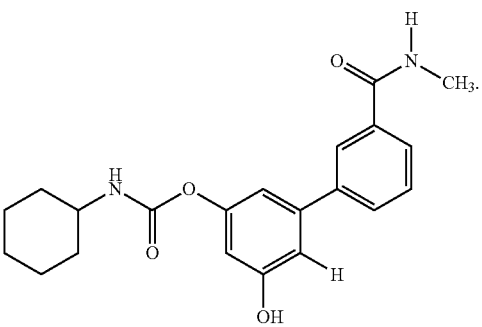 [SMILES: CNC(=O)c1cccc(-c2cc(O)cc(OC(=O)NC3CCCCC3)c2)c1]

In other embodiments, the present invention provides a compound having the following structure:

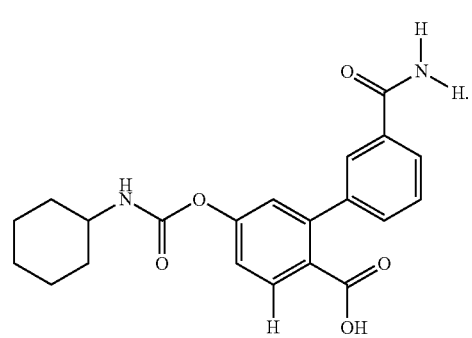

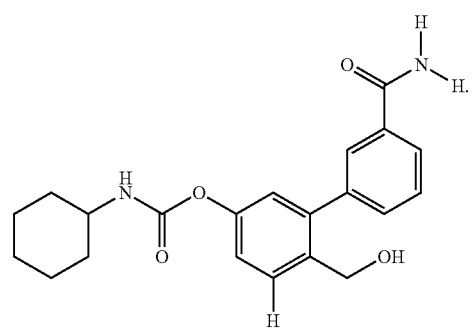

In some other embodiments, the present invention provides a pharmaceutical composition comprising a compound, as set forth above, with a pharmaceutically acceptable excipient. In yet other embodiments, the present invention provides a pharmaceutical composition comprising a pharmaceutically acceptable salt of a compound, as set forth above. In other embodiments, the present invention provides a medicament for treating a disease or condition as set forth herein wherein the medicament includes a compounds as set forth herein.

Compounds of the invention may contain one or more asymmetric centers and can thus occur as racemates and racemic mixtures, single enantiomers, diastereomeric mixtures and individual diastereomers. The present invention is meant to comprehend all such isomeric forms of the inventive compounds.

Compounds of the invention include any diastereoisomers or pairs of any enantiomers. Diastereomers for example, can be obtained by fractional crystallization from a suitable solvent, for example methanol or ethyl acetate or a mixture thereof. The enantiomers may be separated into individual stereoisomers by conventional means, for example by the use of an optically active acid as a resolving agent.

Alternatively, any enantiomer of such a compound of the invention may be obtained by stereospecific synthesis using optically pure starting materials of known configuration.

The compounds of the present invention may have unnatural ratios of atomic isotopes at one or more of their atoms. For example, the compounds may be radiolabeled with isotopes, such as tritium or carbon-14. All isotopic variations of the compounds of the present invention, whether radioactive or not, are within the scope of the present invention.

The instant compounds may be isolated in the form of their pharmaceutically acceptable acid addition salts, such as the salts derived from using inorganic and organic acids. Such acids may include hydrochloric, nitric, sulfuric, phosphoric, formic, acetic, trifluoroacetic, propionic, maleic, succinic, malonic and the like. In addition, certain compounds containing an acidic function can be in the form of their inorganic salt in which the counterion can be selected from sodium, potassium, lithium, calcium, magnesium and the like, as well as from organic bases. The term "pharmaceutically acceptable salts" refers to salts prepared from pharmaceutically acceptable non-toxic bases or acids including inorganic bases or acids and organic bases or acids.

The invention also encompasses prodrugs of the present compounds, which on administration undergo chemical conversion by metabolic processes before becoming active pharmacological substances. In general, such prodrugs will be derivatives of the present compounds that are readily convertible in vivo into a functional compound of the invention. Conventional procedures for the selection and preparation of suitable prodrug derivatives are described, for example, in "Design of Prodrugs", ed. H. Bundgaard, Elsevier, 1985. The invention also encompasses active metabolites of the present compounds.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed by the inventive Formulas.

4. High Throughput FAAH Inhibition Assays

The assays for compounds described herein are amenable to high throughput screening. Preferred assays thus detect binding of the inhibitor to FAAH or the release of a reaction product (e.g., fatty acid amide or ethanolamine) produced by the hydrolysis of a substrate such as oleoylethanolamide or anandamide. The substrate may be labeled to facilitate detection of the released reaction products. High throughput assays for the presence, absence, or quantification of particular reaction products are well known to those of skill in the art. Thus, for example, U.S. Pat. No. 5,559,410 discloses high throughput screening methods for proteins, and U.S. Pat. No. 5,576,220 and U.S. Pat. No. 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

5. Mechanism of Activity

Peripheral cannabinoid receptors exert a powerful inhibitory control over pain initiation, but the endogenous cannabinoid signal that normally engages this intrinsic analgesic mechanism is unknown. It has been found that compound URB937, set forth in the Examples below, which is a novel peripherally restricted inhibitor of fatty acid amide hydrolase (FAAH), the enzyme responsible for the degradation of the endocannabinoid anandamide, suppressed FAAH activity and increased anandamide levels outside the central nervous system (CNS). It is worth noting that URB937 was found to be surprisingly susceptible to a transport system mediated extrusion from brain. Despite a surprising relative inability to access brain and spinal cord, URB937 attenuated behavioral responses indicative of persistent pain in rodent models of inflammation and peripheral nerve injury, and suppresses noxious stimulus-evoked neuronal activation in spinal cord regions implicated in nociceptive processing. $CB_1$ receptor blockade prevents these effects. The results indicated that anandamide-mediated signaling at peripheral $CB_1$ receptors controls the transmission of pain information to the CNS. Accordingly, relatively brain-impermeant FAAH inhibitors, which strengthen this gating mechanism, offer a new approach to pain therapy (see, U.S. Provisional Patent Application Ser. No. 61/368,500, filed on Jul. 28, 2010, which is incorporated herein by reference in its entirety for all purposes, and specifically with respect to methods of assaying FAAH inhibitors for their biological and pharmaceutical properties, and the pharmacological properties of peripherally restricted FAAH inhibitors in general).

Pain perception can be effectively controlled by neurotransmitters that operate within the CNS. This modulation has been well characterized in the dorsal horn of the spinal cord, where impulses carried by nociceptive (pain-sensing) fibers are processed before they are transmitted to the brain. In addition to these central mechanisms, intrinsic control of pain transmission can occur at terminals of afferent nerve fibers outside the CNS. One prominent example of peripheral regulation is provided by the endogenous opioids, which are released from activated immune cells during inflammation and inhibit pain initiation by interacting with opioid receptors localized on sensory nerve endings.

A peripherally restricted FAAH inhibitor is a FAAH inhibitor that does not readily enter the CNS and thus principally interrupts anandamide deactivation only in peripheral tissues. Despite this restricted range of action, peripherally restricted FAAH inhibitors cause marked antinociceptive effects in rodent models of acute and persistent pain, which are prevented by $CB_1$ cannabinoid receptor blockade. These findings indicate that inhibition of peripheral FAAH activity magnifies an endogenous analgesic mechanism which regulates the transmission of emerging nociceptive inputs to the spinal cord and the brain. The mechanism is likely to be mediated by anandamide or another endogenous fatty acid amide cannabinoid.

Peripheral anandamide signaling is thought to serve as a diffuse paracrine system that modulates the intensity of pain stimuli as they arise in damaged tissues. For example, signals generated by inflammation and neural injury can trigger the local release of anandamide. Further, membrane depolarization and activation of TRPV-1 channels each stimulates anandamide production in cultures of sensory neurons, while activation of the proinflammatory receptor, Toll-like receptor 4, causes a similar effect in macrophages. These signals, and others yet to be identified, may contribute to the elevations in peripheral anandamide documented in animal models of spinal nerve injury and inflammation as well as in painful human conditions such as complex regional pain syndrome and arthritis. Also, though particularly abundant in the brain, $CB_1$ receptors are broadly distributed throughout mammalian tissues and organs. In particular, they are expressed in large-sized primary sensory neurons and are transported to peripheral nerve endings, where they may be both necessary to maintain normal pain thresholds and sufficient to exert marked antinociceptive effects. $CB_1$ receptors on pain-sensing terminals may mediate the analgesic actions of locally produced anandamide, and might also be implicated in the anti-inflammatory activity of this lipid mediator through their inhibitory influence on the release of excitatory neuropeptides. Nevertheless, it is reasonable to assume that other cannabinoid and cannabinoid-like receptors also contribute, directly or indirectly, to anandamide signaling in response to injury. Two likely candidates are $CB_2$ receptors, which can be activated either by anandamide, or 2-AG, and type-α peroxisome proliferator-activated receptors, which are activated by PEA and other lipid-derived mediators. These receptors and their endogenous ligands are present in peripheral sensory neurons and immune cells, and have been implicated in the modulation of nociception and inflammation.

Mutant mice in which FAAH is selectively deleted in non-neuronal cells, but is preserved in peripheral and central neurons, display a striking phenotype in which normal nociceptive transmission is accompanied by reduced responsiveness to proinflammatory triggers. A possible explanation for this finding, which is consistent with the present results, is that the signaling activity of anandamide at peripheral nociceptors is regulated by FAAH localized to the nociceptors themselves, rather than to neighboring non-neural cells. This is consistent with the observation that peripheral axotomy induces FAAH expression in large-sized sensory neurons, a response that is expected to expand the colocalization of FAAH with $CB_1$ receptors.

Direct-acting agonists of opioid receptors exert profound analgesic effects in animal and human experimental pain models. The results set forth herein show that is possible to achieve significant analgesia also by magnifying the activity of an anandamide-based mechanism involved in maintaining nociceptive homeostasis. The present invention provides methods for the intrinsic control of pain which can be exploited therapeutically. The present invention also provides methods for developing effective analgesics largely devoid of central side effects. The present invention further provides effective analgesics largely devoid of central side effects.

6. Methods

The compounds and compositions set forth herein are useful for treating disorders in which peripheral FAAH inhibition is desirable. Such disorders include, but are not limited to, pain, inflammation, auto-immune disorders, obesity, eating disorders, and appetite control, metabolic disorders, liver steatosis and asthma. Certain compositions and compounds set forth herein offer a significant advantage over peripherally restricted FAAH inhibitors, such as the compound URB937, which may form a toxic benzoquinone moiety through liver oxidation of the para-hydroxybiphenyl moiety.

In some embodiments, the present invention provides methods of treating disorders including, but are not limited to, pain, inflammation, auto-immune disorders, obesity, eating disorders, and appetite control, metabolic disorders, liver steatosis and asthma, wherein the methods includes administering to a patient in need thereof a pharmaceutical composition having a compound as set forth herein. In other embodiments, the present invention provides methods of treating pain, wherein the methods includes administering to a patient in need thereof a pharmaceutical composition having a compound as set forth herein. In some other embodiments, the present invention provides methods of treating inflammation, wherein the methods includes administering to a patient in need thereof a pharmaceutical composition having a compound as set forth herein. In some embodiments, the present invention provides methods of treating an auto-immune disorder, wherein the methods includes administering to a patient in need thereof a pharmaceutical composition having a compound as set forth herein. In some other embodiments, the present invention provides methods of treating obesity, wherein the methods includes administering to a patient in need thereof a pharmaceutical composition having a compound as set forth herein. In yet other embodiments, the present invention provides methods of treating an eating disorder, wherein the methods includes administering to a patient in need thereof a pharmaceutical composition having a compound as set forth herein. In still other embodiments, the present invention provides methods of treating appetite control, wherein the methods includes administering to a patient in need thereof a pharmaceutical composition having a compound as set forth herein. In certain embodiments, the present invention provides methods of treating a metabolic disorder, wherein the methods includes administering to a patient in need thereof a pharmaceutical composition having a compound as set forth herein. In some embodiments, the present invention provides methods of treating liver steatosis, wherein the methods includes administering to a patient in need thereof a pharmaceutical composition having a compound as set forth herein. In some other embodiments, the present invention provides methods of treating asthma, wherein the methods includes administering to a patient in need thereof a pharmaceutical composition having a compound as set forth herein.

The present invention also sets forth methods wherein FAAH inhibitors greatly accelerate the rate and quality of wound healing. The term wounds as used herein is exemplified but not limited to skin injury. Other types of wounds, as contemplated herein, can involve damage or injury to an internal tissue or organ such as the lung, kidney, heart, gut, tendon or liver. The wounds may be acute (such as, but not limited to, penetrative injuries, burns, nerve damage or elective surgery) or chronic (such as, but not limited to, diabetes, decubitus ulcerations) or occur in healing-compromised individuals (such as, but not limited to, elderly individuals, persons treated with GCs, the malnourished). The wounds may result from trauma, overuse of tissues, surgery, or disease, including injuries to internal organs, the extremities, and skin. In some embodiments, the compounds and compositions set forth herein have wound-healing properties. In certain embodiments, the compounds and compositions set forth herein are useful for accelerating the healing of surgical wounds, diabetic ulcers and, or, pressure ulcers.

Accordingly, in some embodiments, the present invention provides a method of accelerating the rate or the quality of healing of wounds or tissue injuries in a subject in need thereof, said method comprising administering to the subject a therapeutically effective doses of a globally acting and/or peripherally restricted FAAH inhibitor. For instance, the healing can cut the time it takes a wound to heal by 25%, 40%, 60% as compared to an untreated or control wound (e.g., 1, 2, 3, 4, 5, 6, 7, 8, or 9 days less than a control or untreated wound). For instance, the improved quality of healing can provide for a greater retention of function in the wounded tissue or site of injury. In some embodiments, the administering can be topical, local, systemic, oral, subcutaneous, transdermal, rectal, by inhalation, intranasal, intravenous, intramuscular or intra-peritoneal. In any of the above embodiments, the wound or tissue injury can be an acute wound or injury or may be selected from the group consisting of a penetrative injury, a burn, nerve damage, a surgical wound, an injury to an internal organ, a skin injury. In yet more embodiments, the wound or tissue injury can be an acute, chronic, or recurring condition selected from the group consisting of vascular or tissue injuries associated with metabolic diseases (e.g., diabetes, hyperuricemia, calcinosis), autoimmune conditions (e.g., vasculitis, hypodermis gangrenosum, etc.), degenerative lesions (e.g., decubitus, diseases of the connective tissue such as rheumatoid arthritis, systemic lupus erythematosus, scleroderma, mixed connective tissue disease, etc.), lesions caused by infectious diseases (e.g., viral, bacterial, fungal, mixed), cancer lesions (squamous cell carcinomas, melanomas, skin metastases, etc.), and hematological lesions (cryoglobulinemia, thrombocytosis, lymphoproliferative disorders, etc.). The wound or injury can be a penetrating wound or injury to an internal organ. The injured organ may include, but not be limited to, the liver, intestine, stomach, heart, lung, pancreas, kidney, eye, ear, muscle, or bladder. In some further embodiments of such, the FAAH inhibitors are administered to post-surgical patients to promote wound healing.

In still other embodiments, the FAAH inhibitor as set forth herein are formulated for topical administration as a cream, gel, cataplasm, pomade, liniment, milk, lotion, emulsion, spray, collyrium, drops, powder. The FAAH inhibitor can also be incorporated into a dressing or surgical implant (e.g., stent, artificial replacement for a joint, suture). In other embodiments, the FAAH inhibitor is formulated for systemic administration as an injectable solution or a suppository or for oral administration. The FAAH inhibitor can also be formulated as a as suspension, syrup, tablets, capsules, or pill.

In other embodiments, the subjects to be treated by the methods set forth herein are chronic wound patients (e.g., subjects with diabetes or pressure ulcers ['bed sores'] to whom the treatment may be given systemically or locally). In other embodiments, the administering is prophylactic. For instance, an overuse injury to muscle or tendon may be prevented, delayed or avoided by administering a FAAH inhibitor to the subject during and/or before the period of overuse. In some embodiments, the invention provides methods wherein administering the compounds and compositions, as set forth herein, results in a rate of healing which exceeds the rate at which an overuse injury would heal in the absence of the administration of the compounds and compositions set forth herein.

7. Pharmaceutical Compositions

The invention also provides pharmaceutical compositions of the above peripherally restricted FAAH inhibitory compounds. The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. The term "pharmaceutical composition" indicates a composition suitable for pharmaceutical use in a subject, including an animal or human. A pharmaceutical composition generally comprises an effective amount of an active agent and a pharmaceutically acceptable carrier.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend in part on the nature and severity of the conditions being treated and on the nature of the active ingredient. An exemplary route of administration is the oral route. The compositions may be conveniently presented in unit dosage form and prepared by any of the methods well-known in the art of pharmacy.

In practical use, the compounds of the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations can contain at least 0.1 percent of active compound. The percentage of active compound in these compositions may, of course, be varied and may conveniently be between about 2 percent to about 60 percent of the weight of the unit. The amount of active compound in such therapeutically useful compositions is such that a therapeutically effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor. To prevent breakdown during transit through the upper portion of the GI tract, the composition may be an enteric coated formulation.

With respect to formulations with respect to any variety of routes of administration, methods and formulations for the administration of drugs are disclosed in Remington's Pharmaceutical Sciences, 17th Edition, (Gennaro et al. Eds., Mack Publishing Co., 1985). Remington's Pharmaceutical Sciences, Gennaro A R ed. 20th edition, 2000: Williams & Wilkins Pa., USA.

Solid pharmaceutical excipients suitable for use with the present invention include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, and the like). Preferred liquid carriers, particularly for injectable solutions, include water, saline, aqueous dextrose and glycols.

8. Administration

The compounds set forth herein can be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound as set forth herein in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

The compounds of the invention may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The compounds of the invention can be effective over a wide dosage range. For example, in the treatment of adult humans, dosages from about 10 to about 1000 mg, about 100 to about 500 mg or about 1 to about 100 mg may be needed. Doses of the 0.05 to about 100 mg, and more preferably from about 0.1 to about 100 mg, per day may be used. A most preferable dosage is about 0.1 mg to about 70 mg per day. In choosing a regimen for patients, it may frequently be necessary to begin with a dosage of from about 2 to about 70 mg per day and when the condition is under control to reduce the dosage as low as from about 0.1 to about 10 mg per day. For example, in the treatment of adult humans, dosages from about 0.05 to about 100 mg, preferably from about 0.1 to about 100 mg, per day may be used. The exact dosage will depend upon the mode of administration, on the therapy desired, form in which administered, the subject to be treated and the body weight of the subject to be treated, and the preference and experience of the physician or veterinarian in charge.

Generally, the compounds of the present invention can be dispensed in unit dosage form comprising preferably from about 0.1 to about 100 mg of active ingredient together with a pharmaceutically acceptable carrier per unit dosage. Usually, dosage forms suitable for oral, nasal, pulmonary or transdermal administration comprise from about 0.001 mg to about 100 mg, preferably from about 0.01 mg to about 50 mg of the compounds admixed with a pharmaceutically acceptable carrier or diluent. For storage and use, these preparations preferably contain a preservative to prevent the growth of microorganisms.

Administration of an appropriate amount the candidate compound may be by any means known in the art such as, for example, oral or rectal, parenteral, intraperitoneal, intravenous, subcutaneous, subdermal, intranasal, or intramuscular. In some embodiments, administration is transdermal. An appropriate amount or dose of the candidate compound may be determined empirically as is known in the art. An appropriate or therapeutic amount is an amount sufficient to provide the desired therapeutic effect (e.g., treat or alleviate pain or treat or reduce inflammation). The candidate compound can be administered as often as required to alleviate the pain or reduce the inflammation, for example, hourly, every six, eight, twelve, or eighteen hours, daily, or weekly. In some of the methods set forth herein, the methods includes administering a therapeutically effective amount of a compounds which is set forth herein.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Injection solutions and suspensions can be prepared from sterile powders, granules, and tablets of the kind previously described. Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

With respect to transdermal routes of administration, methods for transdermal administration of drugs are disclosed in Remington's Pharmaceutical Sciences, Gennaro A R ed. 20th edition, 2000: Williams & Wilkins Pa., USA. Dermal or skin patches are a preferred means for transdermal delivery of the compounds of the invention. Patches preferably provide an absorption enhancer such as DMSO to increase the absorption of the compounds. Other methods for transdermal drug delivery are disclosed in U.S. Pat. Nos. 5,962,012, 6,261,595, and 6,261,595. Each of which is incorporated by reference in its entirety.

Preferred patches include those that control the rate of drug delivery to the skin. Patches may provide a variety of dosing systems including a reservoir system or a monolithic system, respectively. The reservoir design may, for example, have four layers: the adhesive layer that directly contacts the skin, the control membrane, which controls the diffusion of drug molecules, the reservoir of drug molecules, and a water-resistant backing.

Such a design delivers uniform amounts of the drug over a specified time period, the rate of delivery has to be less than the saturation limit of different types of skin.

The monolithic design, for example, typically has only three layers: the adhesive layer, a polymer matrix containing the compound, and a water-proof backing. This design brings a saturating amount of drug to the skin. Thereby, delivery is controlled by the skin. As the drug amount decreases in the patch to below the saturating level, the delivery rate falls.

Compounds of the invention may be used in combination with other compounds of the invention or with other drugs that may also be useful in the treatment, prevention, suppression of pain, inflammation, or immune disorders. In one embodiment, the second drug is not a FAAH inhibitor and is directed toward the same disorder as the FAAH inhibitor. Such other drugs may be administered, by a route and in an amount commonly used therefor, contemporaneously or sequentially with a compound of the invention. When a compound of the invention is used contemporaneously with one or more other drugs, a pharmaceutical composition in unit dosage form containing such other drugs and the compound is preferred. When used in combination with one or more other active ingredients, the compound of the present invention and the other active ingredients may be used in lower doses than when each is used singly. Accordingly, the pharmaceutical compositions of the present invention include those that contain one or more other active ingredients, in addition to the compounds disclosed above.

In the pharmaceutical compositions of the present invention for oral, sublingual, subcutaneous, intramuscular, intravenous, transdermal, local or rectal administration, the active principle, by itself or in association with another active principle, can be administered to animals and humans in unit forms of administration mixed with conventional pharmaceutical carriers. The appropriate unit forms of administration include oral forms such as tablets, gelatin capsules, powders, granules and solutions or suspensions to be taken orally, sublingual and buccal forms of administration, aerosols, implants, subcutaneous, intramuscular, intravenous, intranasal or intraocular forms of administration and rectal forms of administration.

In other embodiments, the pharmaceutical compositions of the present invention, the active principle or active principles are generally formulated in dosage units. The dosage unit contains from 0.5 to 1000 mg, advantageously from 1 to 500 mg and preferably from 2 to 200 mg of FAAH inhibitor per dosage unit for daily administration.

In some embodiments, the present invention sets forth methods wherein the methods include administering a pharmaceutical composition having a dosage unit of a compound which is set forth herein. In other embodiments, the present invention sets forth pharmaceutical compositions having a dosage unit of a compound which is set forth herein. The dosage unit contains from 0.5 to 1000 mg, advantageously from 1 to 500 mg and preferably from 2 to 200 mg of a compound which is set forth herein. In certain embodiments, the dosage unit is for daily administration. In other embodiments, the dosage unit is for weekly administration. In still other embodiments, the dosage unit is for monthly administration. In still other embodiments, the dosage unit is for an irregular administration. In some embodiments, the dosage unit includes 0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 4.0, 4.5, 5.0, 6.5, 7.0, 7.5, 8.0, 8.5, 9.0, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 200, 250, 300, 350, 400, 450, 500, 550, 600, 650, 700, 750, 800, 850, 900, 950, 975, or 1000 mg of a compound which is set forth herein.

9. Methods of Treatment a. Control of Pain

In some embodiments, the compounds set forth herein may be administered to alleviate or treat pain in a subject. The treatment may be prophylactic or therapeutic. The treatment may be administered to a human subject. The compounds and compositions of the invention may be administered solely for the purposes of reducing the severity or frequency or extent of pain. The treatment may be administered in a combination therapy with another pain reliever or anti-inflammatory agent. In some embodiments, the pain can be a neuropathic pain selected from the group consisting of post trigeminal neuralgia, neuropathic low back pain, peripheral or polyneuropathic pain, complex regional pain syndrome (causalgia and reflex sympathetic dystrophy), diabetic neuropathy, toxic neuropathy, and chronic neuropathy caused by chemotherapeutic agents. In other embodiments, the pain is renal and liver colic pain or fibromyalgia. In some neuropathic pain embodiments, the primary lesion or dysfunction of the nervous system is caused by a mechanical injury to a nerve of the subject. In a further embodiment, the mechanical injury is due to compression of a nerve, transection of nerve, causalgia, spinal cord injury, post surgical pain, phantom limb pain, or scar formation in the subject.

In other embodiments, the pain is a pain caused by inflammation or injury of a tissue. Inflammatory pain develops in response to tissue damage occurring from the noxious stimuli. In response to the tissue injury, cytokines and other mediators are released which strengthen nociception. As a result primary hyperalgesia (increased sensitivity to pain) occurring in the area of injury and a secondary hyperalgesia occurring in the tissue surrounding the injury ensue. The hyperalgesia subsides with the inflammation as the tissue is healed. In some further embodiments, the inflammation is associated with pulmonary edema, kidney stones, minor injuries, wound healing, skin wound healing, vaginitis, candidiasis, lumbar spondylanhrosis, lumbar spondylarthrosis, vascular diseases, migraine headaches, sinus headaches, tension headaches, dental pain, periarteritis nodosa, thyroiditis, aplastic anemia, Hodgkin's disease, sclerodoma, rheumatic fever, type I diabetes, type II diabetes, myasthenia gravis, multiple sclerosis, sarcoidosis, nephrotic syndrome, Behcet's syndrome, polymyositis, gingivitis, hypersensitivity, swelling occurring after injury, or myocardial ischemia, or osteoarthritis.

b. Control of Inflammation

In some embodiments, the compounds of Formula I may be administered to alleviate inflammation in a subject. The treatment may be prophylactic or therapeutic. The treatment may be administered to a human subject. The compounds and compositions of the invention may be administered solely for the purposes of reducing the severity or frequency or extent of the inflammation. The treatment may be administered in a combination therapy with another pain reliever or anti-inflammatory agent.

10. Examples a. Example 1

Methods for Screening Compounds for Antinociceptive Activity

Methods for screening FAAH inhibitors for an antinociceptive effect are well known to one of ordinary in the art. For instance, the test compounds can be administered to the subject animals in the mouse hot-plate test and the mouse formalin test and the nociceptive reactions to thermal or chemical tissue damage measured. See also U.S. Pat. No. 6,326,156 which teaches methods of screening for antinociceptive activity. See Cravatt et al. *Proc. Natl. Acad. Sci. U.S.A.* 98:9371-9376 (2001).

b. Example 2

The Pharmacological Profile of Peripherally Restricted FAAH Inhibitors:

Materials and Methods include the following.

Enzyme Assays:

Standard FAAH and monoacylglycerol lipase assays were conducted as described (Clapper, J. R. et al., A second generation of carbamate-based fatty acid amide hydrolase inhibitors with improved activity in vivo. ChemMedChem 4 (9), 1505-1513 (2009); King, A. R. et al., URB602 inhibits monoacylglycerol lipase and selectively blocks 2-arachidonoylglycerol degradation in intact brain slices. Chem Biol 14 (12), 1357-1365 (2007)), using as substrates [$^3$H]-anandamide (a gift of the National Institute on Drug Abuse) and 2-oleoyl-sn-glycerol (Nu-Check Prep, Elysian, Minn.), respectively.

Tissue Analyses:

Tissue extractions and liquid chromatography/mass spectrometry analyses of endocannabinoids was performed as described (Astarita, G., Ahmed, F., & Piomelli, D., Identification of biosynthetic precursors for the endocannabinoid anandamide in the rat brain. J Lipid Res 49 (1), 48-57 (2008)).

Carrageenan-Induced Inflammation in Mice:

Peripheral inflammation was induced by intraplantar (i.pl.) injection of the polysaccharide λ-carrageenan (i.pl. 1% weight vol$^{-1}$ in sterile water, 20 μL) into the left hind paw of male CD1 mice. Carrageenan-treated mice received compound 1 (10, 30 mg/kg, per os) just before intraplantar injection of carrageenan.

Behavioral Tests:

Nocifensive responses were measured elicited by intraplantar injection of carrageenan in male CD1 mice (LoVerme, J., La Rana, G., Russo, R., Calignano, A., & Piomelli, D., The search for the palmitoylethanolamide receptor. Life Sci 77 (14), 1685-1698 (2005)).

Chemicals

[$^3$H]-Anandamide was purchased from American Radiolabeled Chemicals, Inc. (St. Louis, Mo.). Anandamide, [$^2$H$_4$]-anandamide and PEA were synthesized in the laboratory (Fegley, D. et al., Characterization of the fatty acid amide hydrolase inhibitor cyclohexyl carbamic acid 3'-carbamoyl-biphenyl-3-yl ester (URB597): effects on anandamide and oleoylethanolamide deactivation. J Pharmacol Exp Ther 313 (1), 352-358 (2005)). N-cyclohexyl biphenyl-3-ylacetamide was donated by Kadmus Pharmaceuticals Inc.

Animals

Male Swiss Webster and CD1 mice (Charles River, 20-30 g) were used. Mice were group-housed in standard cages at room temperature on a 12:12 h light:dark cycle with unlimited access to water and standard chow pellets. Wistar rats were typically used for the FAAH studies. All experiments met the National Institutes of Health guidelines for the care and use of laboratory animals, were approved by the Institutional Animal Care and Use Committee of the University of California, Irvine, and the University of Georgia, Athens, and were in compliance with the European Community Council Directive 86 (609) EEC and the experimental protocol was carried out in compliance with Italian regulations (DL 116/92).

Tissue Extractions

Mice were sacrificed with isoflurane and tissues were collected and immediately frozen in liquid nitrogen. Frozen tissues were weighed and homogenized in methanol (1 mL) containing $[^2H_4]$-anandamide, $[^2H_4]$-PEA, $[^2H_8]$-2-AG, and N-cyclohexyl biphenyl-3-ylacetamide as internal standards. Analytes were extracted with chloroform (2 vol) and washed with water (1 vol). Organic phases were collected and dried under nitrogen. For other analyses the organic extract was fractionated by open-bed silica gel column chromatography, as described (Cadas, H., di Tomaso, E., & Piomelli, D., Occurrence and biosynthesis of endogenous cannabinoid precursor, N-arachidonoyl phosphatidylethanolamine, in rat brain. J Neurosci 17 (4), 1226-1242 (1997)). Briefly, the extract was dissolved in chloroform and loaded onto small glass columns packed with Silica Gel G (60~A 230-400 Mesh ASTM; Whatman, Clifton, N.J.). Anandamide, PEA and 2-AG were eluted with chloroform/methanol (9:1, vol/vol).

Serum Extractions

Trunk blood was collected from decapitated mice, allowed to clot and placed on ice. The clotted blood was centrifuged at 18,000×g for 10 min at 4° C. and the serum was transferred to glass vials and diluted with distilled water to 1 mL.

Proteins were precipitated with ice-cold acetone (1 mL) containing N-cyclohexyl biphenyl-3-ylacetamide as an internal standard, and the precipitate was removed by centrifugation at 3000×g for 10 min at 4° C. The samples were dried under nitrogen to remove acetone, and extracted with chloroform/methanol as described above.

Drug Preparation for In Vivo Experiments

Drugs were dissolved in polyethylene glycol 400/Tween-80/saline (1/1/18; by volume) and administered by i.p. (5-10 mL-kg$^{-1}$). Alternatively, drugs were dissolved in polyethylene glycol 400/Tween-80/saline (Oct. 10, 1980; by volume) and administered per os (10 and 30 mg/Kg).

Behavioral Tests

Paw edema was induced in mice by injection into the right hind paws of 50 μL, of sterile saline containing 1% λ-carrageenan. Paw volumes were measured using a plethysmometer (Ugo Basile, Milan, Italy). Vehicle or compound 1 (10 and 30 mg kg$^{-1}$, per os) were administered immediately before carrageenan. The increase in paw volume (mL) was evaluated as the difference between the paw volume measured at each time point and the basal paw volume measured immediately before carrageenan injection.

Mechanical Hyperalgesia—

Mechanical hyperalgesia was determined by measuring the latency in seconds to withdraw the paw away from a constant mechanical pressure exerted onto the dorsal surface. A 15 g calibrated glass cylindrical rod (diameter=10 mm) chambered to a conical point (diameter=3 mm) was used to exert the mechanical force. The weight was suspended vertically between two rings attached to a stand and was free to move vertically. A cutoff time of 180 s was used. Withdrawal threshold was measured on the inflamed ipsilateral paw at different time points after oral drug administration. Six mice were included in each experimental group. Three determinations were made on each mice resulting in a total of 18 measurements. Thermal hyperalgesia was assessed as described (Hargreaves, K., Dubner, R., Brown, F., Flores, C., & Joris, J., A new and sensitive method for measuring thermal nociception in cutaneous hyperalgesia. Pain 32 (1), 77-88 (1988)), measuring the latency to withdraw the hindpaw from a focused beam of radiant heat (thermal intensity: infrared 3.0) applied to the plantar surface using a plantar test apparatus (Ugo Basile, Italy). The cutoff time was set at 30 s. Withdrawal latency was measured on the inflamed ipsilateral paw at different time points after oral drug administration. Six mice were included in each experimental group. Three determinations were made on each mice resulting in a total of 18 measurements.

Statistical Analyses:

Results are expressed as the mean±s.e.m. Statistical significance was determined by Students t test, one-way, or two-way analysis of variance (ANOVA) followed by Bonferroni post hoc test when appropriate. Post hoc comparisons that did not meet the equal variance assumption were corrected by fractional adjustment of the degrees of freedom. Analyses were performed using SPSS statistical software (version 17.0; SPSS Incorporated, Chicago, Ill., USA).

General Analytical Methods:

UPLC/MS analyses of compounds were run on a Waters ACQUITY UPLC/MS instrument consisting of a SQD Single Quadropole Mass Spectrometer equipped with an electrospray ionization interface and a photodiode array detector. The analyses were performed on an ACQUITY UPLC BEH C18 column (50×2.1 mmID, particle size 1.7 μm) with a VanGuard BEH C18 pre-column (5×2.1 mmID, particle size 1.7 μm). The mobile phases were 10 mM ammonium acetate at pH 5 adjusted with acetic acid (A) and 10 mM ammonium acetate in acetonitrile-water (95:5) at pH 5 (B). Electrospray ionization in positive and negative mode was used in the mass scan range 100-500 Da.

NMR experiments were run on a Bruker Avance III 400 system (400.13 MHz for $^1H$), equipped with a BBI inverse probe and Z-gradients. Unless indicated, spectra were acquired at 300 K, using deuterated dimethylsulfoxyde (DMSO-d$_6$) and deuterated chloroform (CDCl$_3$) as solvents.

c. Example 3

Synthesis of [3-(3-carbamoylphenyl)-5-hydroxy-phenyl]N-cyclohexylcarbamate (Compound 1)

Compound 1 was synthesized as described in the following Scheme:

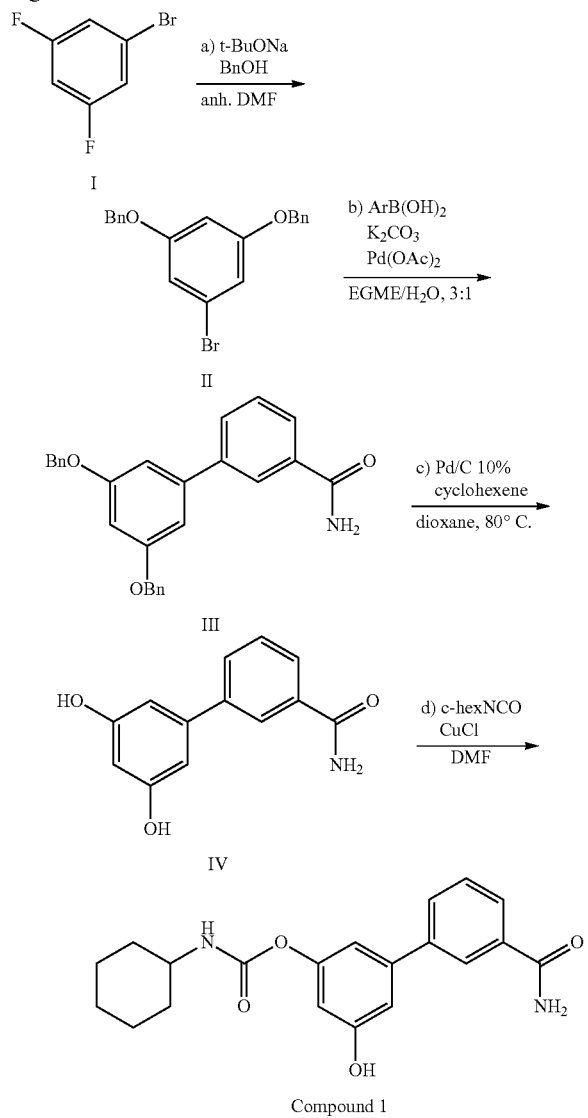

Step 1: 1,3-dibenzyloxy-5-bromo-benzene (II): In a 1 L round bottomed flask, equipped with a magnetic stirrer and under nitrogen atmosphere, 200 mL of anhydrous dimethylformamide (DMF) were loaded followed by the addition of t-BuONa (5 eq., 207.3 mmol, 19.9 g) and, subsequently, benzyl alcohol (5 eq., 207.3 mmol, 21.3 mL). After 10 min, I (1 eq., 41.5 mmol, 4.8 mL) was added and the reaction mixture was heated at 90° C. After 3 h, the reaction mixture was cooled to room temperature and slowly transferred, under stirring, in a 3 L flask, containing 600 mL of water and 500 mL of methyl-t-butyl ether (MTBE). After 30 min, the organic phase was separated, washed with water (400 mL) and dried over $Na_2SO_4$. Evaporation of the solvent gave II as yellow oil that crystallized after cooling overnight at −19° C. The solid was treated with 180 mL of MeOH then filtered and washed with 30 mL of cold MeOH (11 g, 72% yield). $^1$H NMR (400 MHz, CDCl$_3$) δ 7.52-7.31 (m, 10H), 6.80 (d, J=2.2 Hz, 2H), 6.57 (t, J=2.2 Hz, 1H), 5.03 (s, 4H). MS (ESI): 367 (M−H)$^-$, 369 (M+2H)$^-$.

Step 2: 3-(3,5-dibenzyloxyphenyl)benzamide (III): To a solution of 1,3-dibenzyloxy-5-bromo-benzene (II) (1 eq., 29.8 mmol, 11.0 g) in ethylene glycol monomethyl ether (EGME) (152 mL) in a 500 mL round bottomed flask, water (54 mL) was added drop wise, followed by the addition of $K_2CO_3$ (2 eq., 59.6 mmol, 8.2 g), 3-carbamoylbenzeneboronic acid (1.5 eq., 44.7 mmol, 7.4 g) and Pd(OAc)$_2$ (1.2%, 0.36 mmol, 80.3 mg). The reaction mixture was stirred at 60° C. for 20 min. Then 100 mL of water were added and a precipitate was formed which was filtered and washed with water (50 mL). The title compound was recrystallized from 350 mL of a 5:2 mixture of MeOH/THF (8.5 g, 70% yield). $^1$H NMR (400 MHz, DMSO-d6) δ 8.15 (t, J=1.8 Hz, 1H), 8.12 (bs, 1H), 7.87 (d, J=7.8 Hz, 1H), 7.83 (d, J=7.8 Hz, 1H), 7.61-7.30 (m, 12H), 7.00 (d, J=2.2 Hz, 2H), 6.73 (t, J=2.2 Hz, 1H), 5.19 (s, 4H). MS (ESI): 410 (M+H)$^+$, 408 (M−H)$^-$.

Step 3: 3-(3,5-dihydroxyphenyl)benzamide (IV): To a suspension of 3-(3,5-dibenzyloxyphenyl)benzamide III (8.5 g, 20.8 mmol) in 260 mL of dioxane, in a 500 mL three necked round bottomed flask, 80 mL of cyclohexene were added and the mixture was heated at 50° C. for 15 min to ensure complete dissolution of the solids. The mixture was then cooled to room temperature and 2 g of Pd/C 10% were added. The reaction mixture was heated at 80° C. for 2 h and an additional amount of 2 g of Pd/C were then added. After 2 h, the mixture was cooled down to room temperature, then filtered through a small pad of celite and washed with 100 mL of dioxane and 100 mL of absolute ethanol. The clear solution was concentrated to dryness to afford IV as a fluffy light yellow solid (4.8 g, quantitative). $^1$H NMR (400 MHz, DMSO-d6) δ 9.38 (s, 2H), 8.10 (bs, 1H), 8.07-8.03 (m, 1H), 7.83 (d, J=7.8 Hz, 1H), 7.68 (d, J=7.8 Hz, 1H), 7.50 (t, J=7.7 Hz, 1H), 7.38 (bs, 1H), 6.55 (d, J=2.1 Hz, 2H), 6.27 (t, J=2.1 Hz, 1H). MS (ESI): 230 (M+H)$^+$, 228 (M−H)$^-$.

Step 4: [3-(3-carbamoylphenyl)-5-hydroxy-phenyl]N-cyclohexylcarbamate, Compound 1: To a solution of 3-(3,5-dihydroxyphenyl)benzamide IV (1 eq., 11.4 mmol, 2.6 g) in anhydrous DMF (30 mL) in a 500 mL round bottomed flask CuCl (1 eq., 11.4 mmol, 1.1 g) was added. Cyclohexyl isocyanate (1 eq., 11.4 mmol, 1.45 mL) was then added and the mixture was stirred at room temperature for 30 min. To this solution, 200 mL of a mixture of 3% aq. citric acid solution and 100 mL of ethyl acetate (EtOAc) were then added. The organic phase was separated and dried over $Na_2SO_4$. Evaporation of the solvent gave a crude, which was purified by column chromatography (cyclohexane/EtOAc) to afford compound 1 as white solid. The solid was re-dissolved in 75 mL of a 65:20:15 mixture of water/acetone/ethanol. To this solution 30 mL of water were then added to give a precipitate which was filtered to afford compound 1 as white solid (1.17 g, 29% yield). $^1$H NMR (400 MHz, DMSO-d$_6$) δ 9.86 (s, 1H), 8.13 (bs, 1H), 8.11-8.09 (m, 1H), 7.86 (d, J=7.7 Hz, 1H), 7.75 (d, J=7.7 Hz, 1H), 7.70 (d, J=7.7 Hz, 1H), 7.53 (t, J=7.7 Hz, 1H), 7.41 (bs, 1H), 6.95 (t, J=1.9 Hz, 1H), 6.89 (t, J=1.9 Hz, 1H), 6.53 (d, J=1.9 Hz, 1H), 3.46-3.32 (m, 1H), 1.99-1.46 (m, 6H), 1.46-0.99 (m, 4H). MS (ESI): 355 (M+H)$^+$, 372 (M+NH$_4$)$^+$, 353 (M−H)$^-$.

Synthesis of [3-hydroxy-5-[3-(methylcarbamoyl)phenyl]phenyl]N-cyclohexylcarbamate, Compound 2. Compound 2 was synthesized using a synthetic procedure analogous to the one previously described. $^1$H NMR (400 MHz, DMSO-d6) δ 9.79 (bs, 1H), 8.57 (q, J=4.4 Hz, 1H), 8.07-8.01 (m, 1H), 7.82 (d, J=7.7 Hz, 1H), 7.74 (d, J=7.7 Hz, 1H), 7.69 (d, J=7.9 Hz, 1H), 7.53 (t, J=7.7 Hz, 1H), 6.98-6.92 (m, 1H), 6.91-6.86 (m, 1H), 6.53 (t, J=2.1 Hz, 1H), 3.39-3.31 (m, 1H), 2.82 (d, J=4.4 Hz, 3H), 1.90-1.48 (m, 5H), 1.35-1.04 (m, 5H). MS (ESI): 369 (M+H), 386 (M+NH$_4^+$); 367 (M−H), 427 (M+AcO$^-$).

d. Example 4

Comparison of compounds according to the invention with other peripherally restricted FAAH inhibitors for their ability to inhibit FAAH in the periphery. Using similar FAAH inhibition bioassay methods as described for URB937 above (see, also, Clapper et al. Nature Neuroscience 13:1265-70 (2010)), which is incorporated herein by reference with respect to such FAAH bioassay methods, the hepatic and CNS FAAH inhibitory activities of the compounds following administration was compared to that of URB937. In particular, (1) IC$_{50}$ values were generated in vitro using a FAAH assay. Percent in vivo FAAH inhibition values for (2) liver and (3) brain were determined, as follows. Mice received a 1 mg/kg dose of each compound by the intraperitoneal route, and were killed 2 h after administration. Tissues were collected and FAAH activity was measured ex vivo in tissue extracts (membrane fraction) using the FAAH assay. Data are reported in the Table 1 below.

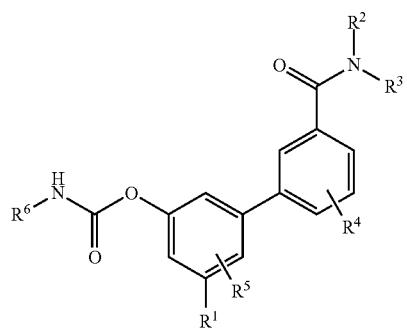

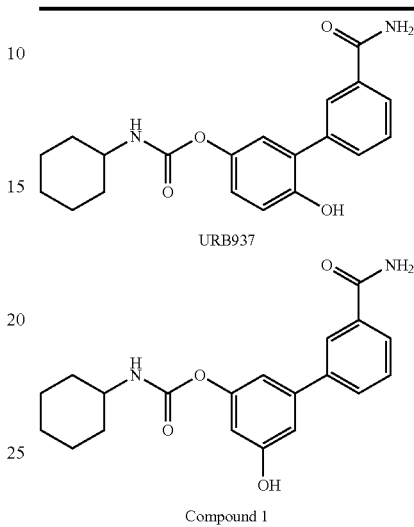

URB937

Compound 1

Based upon their peripheral and central FAAH activities, the Applicants have surprisingly found that placement of a polar substituent on the meta position of the proximal biphenyl ring also provides a peripherally restricted inhibitor of FAAH. Compound 1, and the other compounds of formula I, also are expected to have an important practical advantage in that the metabolism of these compounds in vivo is likely much less able to lead to the formation of a potentially toxic parabenzoquinones.

e. Example 5

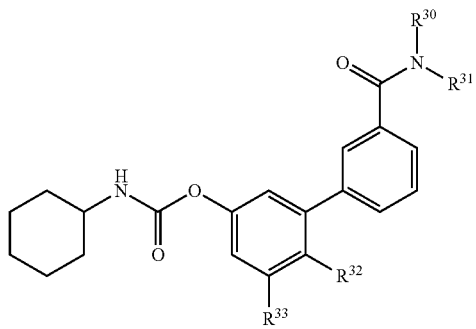

TABLE 1

| # | R$^1$ | R$^2$ | R$^3$ | R$^4$ | R$^5$ | R$^6$ | IC$_{50}$ (nM) | FAAH inhibition in liver (%) | FAAH inhibition in brain (%) |
|---|---|---|---|---|---|---|---|---|---|
| 1 | OH | H | H | H | H | cyclohexyl | 0.8 | 89.5 ± 1.1 | −4.2 ± 2.5 |
| 2 | OH | CH$_3$ | H | H | H | cyclohexyl | 0.3 | 69.1 ± 3.5 | −1.7 ± 0.2 |
| 5 | OCH$_3$ | H | H | H | H | cyclohexyl | 2.5 | 85.8 ± 2.4 | 82.5 ± 0.4 |

TABLE 1-continued

| # | R$^1$ | R$^2$ | R$^3$ | R$^4$ | R$^5$ | R$^6$ | IC$_{50}$ (nM) | FAAH inhibition in liver (%) | FAAH inhibition in brain (%) |
|---|---|---|---|---|---|---|---|---|---|
| URB-937 | H | H | H | H | OH | cyclohexyl | 3 | 91.7 ± 0.7 | −3.0 ± 8.0 |

TABLE 2

| Compound | R$^{30}$ | R$^{31}$ | R$^{32}$ | R$^{33}$ | IC$_{50}$ (nM) | FAAH inhibition in liver (%) | FAAH inhibition in brain (%) |
|---|---|---|---|---|---|---|---|
| URB937 | H | H | OH | H | 3.0 | 91.7 ± 0.7 | −3.0 ± 8.0 |
| ARN1289 | H | H | H | OH | 0.8 | 89.5 ± 1.1 | −4.2 ± 2.5 |
| ARN14427 | H | CH$_3$ | H | OH | 0.3 | 69.1 ± 3.5 | −1.7 ± 0.2 |
| ARN0715 | H | H | COOH | H | 2100 | 86.3 ± 1.3 | −2.1 ± 0.5 |
| ARN0716 | H | H | CH$_2$OH | H | 9.4 | 91.5 ± 1.1 | 10.5 ± 1.5 | f. Example 6

The activity of compounds of Formula I as peripherally restricted FAAH inhibitors was found based in part on the polarity of the p-hydroxyphenyl moiety. It was found that this moiety is a contributor to the peripheral segregation of URB937, a model peripherally restricted FAAH inhibitor. Table 3 shows that analogs in which the $R^{40}$ substituent was weakly polar or apolar—compounds, e.g., 1c, 1d and 1e, were found to enter the brain after systemic administration in mice, whereas an analog in which $R^{40}$ consisted of a polar amino group, e.g., compound 1f, was found to be largely excluded.

TABLE 3

In vitro and in vivo characterization of O-arylcarbamate FAAH inhibitors

| Compound | $R^{40}$ | $IC_{50}$ (nM)[a] | FAAH Inhibition in liver (%)[b] | FAAH Inhibition in brain (%)[b] |
|---|---|---|---|---|
| 1a (URB597) | H | 7.7 ± 1.5 | N.D. | 96.2 ± 0.4 |
| 1b (URB937) | OH | 26.8 ± 4.9 | 91.7 ± 0.7 | −3.0 ± 8.0 |
| 1c | $OCH_3$ | 45.3 ± 14.1 | 94.6 ± 0.7 | 86.4 ± 2.1 |
| 1d | $CH_3$ | 20.5 ± 0.6 | 93.0 ± 1.1 | 91.9 ± 1.5 |
| 1e | F | 49.7 ± 5.8 | 90.7 ± 1.2 | 89.7 ± 1.3 |
| 1f | $NH_2$ | 42.5 ± 4.2 | 92.2 ± 0.6 | 23.2 ± 2.1 |

[a]$IC_{50}$ measured in membrane preparation of rat brain
[b]FAAH inhibition measured ex vivo 1 h after a single injection in mice (1 mg-kg$^{-1}$, i.p.).

The following examples are provided for illustrative purposes, and are not intended to limit the scope of the invention as claimed herein. Any variations in the exemplified compounds, compositions, and, or, methods which occur to the skilled artisan are intended to fall within the scope of the present invention. Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound having the formula:

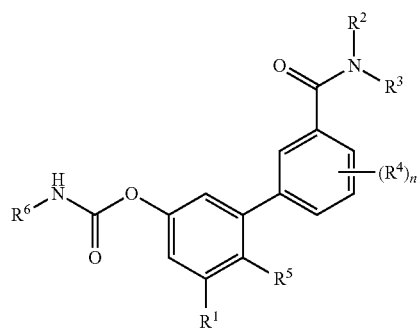

Formula I wherein:
$R^1$ is selected from the group consisting of hydrogen, hydroxy and the physiologically hydrolyzable esters thereof, carboxy and the physiologically hydrolysable esters thereof, hydroxyl-$(C_1$-$C_3)$alkyl and the physiologically hydrolyzable esters thereof, and —$NR^7R^8$, wherein $R^7$ and $R^8$ are independently selected from hydrogen or $(C_1$-$C_3)$alkyl and $R^9$ is selected from hydrogen, methyl, ethyl, trifluoromethyl or trifluoroethyl;
$R^2$ and $R^3$ are independently selected from the group consisting of hydrogen and unsubstituted $(C_1$-$C_3)$alkyl;
each $R^4$ is independently selected from the group consisting of hydrogen and unsubstituted $(C_1$-$C_3)$alkyl and n is an integer from 0 to 4;
$R^5$ is hydrogen, carboxy and the physiologically hydrolysable esters thereof, or hydroxyl-$(C_1$-$C_3)$alkyl and the physiologically hydrolyzable esters thereof,
$R^6$ is an unsubstituted or substituted cyclohexyl, cyclopentyl, cyclobutyl or tetrahydropyran-4-yl;
or a pharmaceutically acceptable salt thereof,
wherein only one of $R^1$ and $R^5$ is hydrogen.

2. The compound of claim 1, wherein $R^2$ and $R^3$ are each H.

3. The compound of claim 1, wherein $R^6$ is unsubstituted.

4. The compound of claim 1, wherein $R^6$ is cyclohexyl.

5. The compound of claim 1, wherein, $R^7$ and $R^8$ are each H.

6. The compound of claim 1, wherein n is 0 or 1.

7. The compound of claim 1, wherein each member of the $R^1$, $R^6$, $R^7$, and $R^8$ Markush groups is unsubstituted.

8. The compound of claim 1, wherein $R_1$ is hydroxy or a physiologically hydrolysable ester thereof.

9. The compound of claim 8, wherein the physiologically hydrolysable ester is of the formula —OC(O)$R^{10}$ and $R^{10}$ is substituted or unsubstituted hydrocarbyl.

10. The compound of claim 1, wherein $R^5$ is COOH or $CH_2OH$.

11. A pharmaceutical composition comprising the compound of claim 1 and a pharmaceutically acceptable carrier.

12. A method of treating a condition selected from the group consisting of pain and inflammation in a mammal in need thereof, comprising administering to the mammal an effective amount of a compound of claim 1.

13. The compound of claim 1, wherein $R^1$ is hydrogen; and $R^5$ is independently hydroxyl-$(C_1$-$C_3)$alkyl or the physiologically hydrolyzable esters thereof or carboxy or the physiologically hydrolysable esters thereof.

14. The compound of claim 1 wherein $R^1$ is hydroxy or the physiologically hydrolyzable esters thereof, carboxy or the physiologically hydrolysable esters thereof, hydroxyl-$(C_1-C_3)$alkyl or the physiologically hydrolyzable esters thereof, —$NR^7R^8$, $R^7$ and $R^8$ are independently selected from hydrogen or $(C_1-C_3)$alkyl; and $R^5$ is hydrogen.

15. The compound of claim 1, wherein $R^5$ is COOH or a physiologically hydrolyzable ester thereof.

16. The compound of claim 1, wherein $R^5$ is $CH_2OH$, or a physiologically hydrolyzable ester thereof.

17. The compound of claim 1, wherein the compound has the formula:

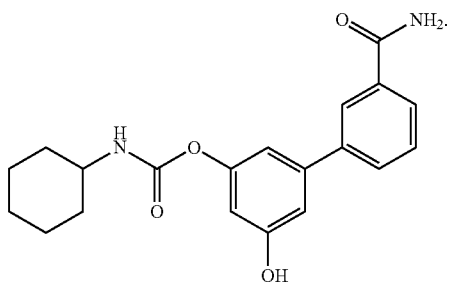 [SMILES: NC(=O)c1cccc(-c2cc(O)cc(OC(=O)NC3CCCCC3)c2)c1]

18. The compound of claim 1, wherein the compounds has the formula:

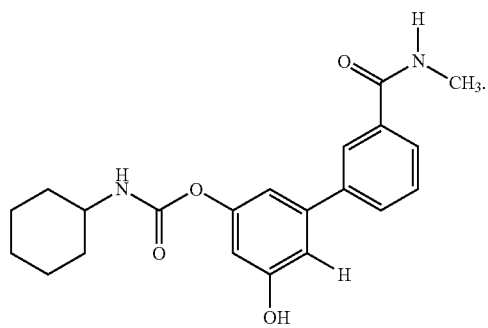 [SMILES: CNC(=O)c1cccc(-c2cc(O)cc(OC(=O)NC3CCCCC3)c2)c1]

19. The compound of claim 1, wherein the compounds has the formula:

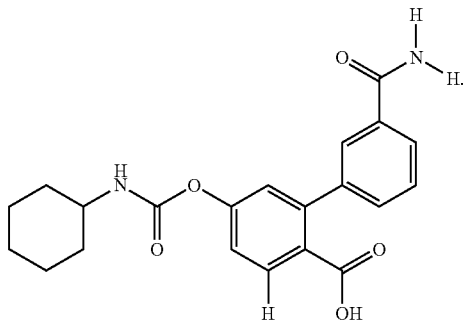

20. The compound of claim 1, wherein the compounds has the formula:

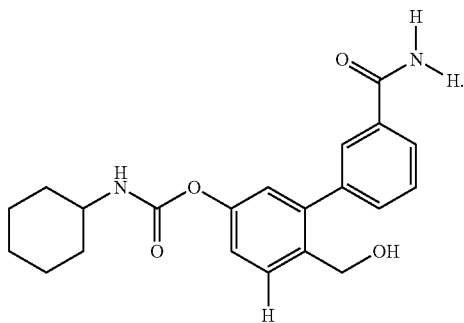

* * * * *